US011491167B2

(12) United States Patent
Yang et al.

(10) Patent No.: US 11,491,167 B2
(45) Date of Patent: Nov. 8, 2022

(54) COMBINATION PRODUCT OF BCL-2 INHIBITOR AND CHEMOTHERAPEUTIC AGENT AND USE THEREOF IN THE PREVENTION AND/OR TREATMENT OF DISEASES

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Guangfeng Wang, Suzhou (CN)

(73) Assignee: ASCENTAGE PHARMA (SUZHOU) CO., LTD., Jiangsu (CN)

(*) Notice: Subject to any disclaimer, the term of this patent is extended or adjusted under 35 U.S.C. 154(b) by 0 days.

(21) Appl. No.: 16/648,597

(22) PCT Filed: Jul. 22, 2019

(86) PCT No.: PCT/CN2019/097081
§ 371 (c)(1),
(2) Date: Mar. 18, 2020

(87) PCT Pub. No.: WO2020/024834
PCT Pub. Date: Feb. 6, 2020

(65) Prior Publication Data
US 2021/0137949 A1    May 13, 2021

(30) Foreign Application Priority Data
Jul. 31, 2018  (CN) .......................... 201810862169.6

(51) Int. Cl.
*A61K 31/635*    (2006.01)
*A61P 35/04*    (2006.01)
*A61K 45/06*    (2006.01)

(52) U.S. Cl.
CPC ............ *A61K 31/635* (2013.01); *A61K 45/06* (2013.01); *A61P 35/04* (2018.01)

(58) Field of Classification Search
CPC .............. A61K 31/4745; A61K 31/496; A61K 31/635; A61K 9/0014; A61K 9/0019; A61K 9/0053; A61K 9/16; A61K 9/20; A61K 9/48; A61K 2300/00; C07D 471/04; A61P 35/00; A61P 35/02; A61P 35/04
See application file for complete search history.

(56) References Cited

U.S. PATENT DOCUMENTS

| 7,432,304 | B2 * | 10/2008 | Wang ..................... A61P 35/04 514/682 |
| 8,546,399 | B2 | 10/2013 | Bruncko et al. |
| 10,213,433 | B2 | 2/2019 | Catron et al. |
| 10,221,174 | B2 | 3/2019 | Wang et al. |
| 2010/0152183 | A1 * | 6/2010 | Bruncko ............... C07D 209/32 514/234.5 |
| 2010/0305122 | A1 | 12/2010 | Bruncko et al. |
| 2011/0124628 | A1 | 5/2011 | Bruncko et al. |
| 2012/0028925 | A1 | 2/2012 | Tao et al. |
| 2012/0157470 | A1 | 6/2012 | Catron et al. |
| 2015/0329541 | A1 | 11/2015 | Bruncko et al. |
| 2016/0287592 | A1 * | 10/2016 | Chang .................... A61K 45/06 |

FOREIGN PATENT DOCUMENTS

| CN | 101918420 A | 12/2010 |
| CN | 104768581 A | 7/2015 |
| CN | 104906100 A | 9/2015 |
| CN | 103402521 B | 1/2016 |
| CN | 105246882 A | 1/2016 |
| CN | 105061315 B | 10/2017 |
| CN | 106794171 B | 3/2020 |
| JP | 2013526612 A | 6/2013 |
| JP | 2013540823 A | 11/2013 |
| JP | 2013543894 A | 12/2013 |
| WO | WO 2005/049593 A2 | 6/2005 |
| WO | WO 2008/030836 A2 | 3/2008 |
| WO | WO 2008/070663 A2 | 6/2008 |
| WO | WO 2010/065824 A2 | 6/2010 |
| WO | WO 2010/065865 A2 | 6/2010 |
| WO | WO 2010/093742 A1 | 8/2010 |
| WO | WO 2010/138588 A2 | 12/2010 |
| WO | WO 2011/068863 A1 | 6/2011 |
| WO | WO 2011/149492 A1 | 12/2011 |
| WO | WO 2012/058392 A1 | 5/2012 |
| WO | WO 2012/071374 A1 | 5/2012 |
| WO | WO 2012/103059 A2 | 8/2012 |
| WO | WO 2014/113413 A1 | 7/2014 |
| WO | WO 2015/130585 A1 | 9/2015 |
| WO | WO 2015/161032 A1 | 10/2015 |
| WO | WO 2016/024230 A1 | 2/2016 |
| WO | WO 2016/188935 A1 | 12/2016 |

(Continued)

OTHER PUBLICATIONS

Adams et al., "The Bcl-2 apoptotic switch in cancer development and therapy," *Oncogene*, 26(9), pp. 1324-1337, (2007).
Adams et al., "The Bcl-2 protein family: arbiters of cell survival," *Science*, 281 (5381), pp. 1322-1326, (1998).
Ackler et al., "The Bcl-2 inhibitor ABT-263 enhances the response of multiple chemotherapeutic regimens in hematologic tumors in vivo." *Cancer Chemotherapy and Pharmacology.*, vol. 66, No. 5, (Jan. 2010), pp. 869-880.
Aguilar et al., "Discovery of 4-((3'R,4'S,5'R)-6"-Chloro-4' -(3-chloro-2-fluorophenyl)-1'-ethyl-2" - oxodispiro[cyclohexane-l,2' -pyrrolidine-3',3" -indoline]-5'-carboxamido)bicycle[2,2,2]octane-1-carboxylic Acid (AA-115/APG-115): A Potent and Orally Active Murine Double Minute 2 (MDM2) Inhibitor in Clinical Development," *J. Med. Chem.* 2017, 60, pp. 2819-2839.

(Continued)

*Primary Examiner* — Sarah Pihonak
(74) *Attorney, Agent, or Firm* — Barnes & Thornburg LLP

(57) ABSTRACT

The present invention relates to a combination product comprising a Bcl-2 inhibitor and a chemotherapeutic agent, and the combination product provides a use in the prevention and/or treatment of diseases (e.g., cancer).

11 Claims, 2 Drawing Sheets

(56) References Cited

FOREIGN PATENT DOCUMENTS

| WO | WO 2017/037579 A1 | 3/2017 |
|----|-------------------|--------|
| WO | WO 2018/027097 A1 | 2/2018 |
| WO | WO 2020/024820 A1 | 2/2020 |
| WO | WO 2020/024826 A1 | 2/2020 |
| WO | WO 2020/024834 A1 | 2/2020 |
| WO | WO 2020/024916 A1 | 2/2020 |
| WO | WO 2020/103921 A1 | 5/2020 |

OTHER PUBLICATIONS

Amundson et al., "An informatics approach identifying markers of chemosensitivity in human cancer cell lines," Cancer Res., 60(21), pp. 6101-6110, (2000).
Bai L., et al., "BM-1197: A Novel and Specific Bcl-2/Bcl-xL Inhibitor Inducing Complete and Long-Lasting Tumor Regression In Vivo," PloS ONE, vol. 9, No. 6, (Jun. 2014), pp. 399404-e99404.
Bingham et al., "Over one hundred solvates of sulfathiazole," Chem. Commun., pp. 603-604, (2001).
Bogenberger et al., "Combined venetoclax and alvocidib in acute myeloid Teukemia," Oncotarget., vol. 8, No. 63, (Nov. 2017), pp. 107206-107222.
Caira et al., "Preparation and crystal characterization of a polymorph, a monohydrate, and an ethyl acetate solvate of the antifungal fluconazole," J. Pharm. Sci., 93(3), pp. 601-611, (2004).
Cang et al., "ABT-199 (venetoclax) and BCL-2 inhibitors in clinical development," J. Hematol. Oncol., 8, pp. 129, (2015).
Chen et al., "The Bcl-2/Bcl-X-L/Bcl-w Inhibitor, Navitoclax, Enhances the Activity of Chemotherapeutic Agents In Vitro and In Vivo," Molecular Cancer Therapeutics., vol. 11, No. 12, (Sep. 2011), pp. 2340-2349.
Danial et al., "Cell death: critical control points," Cell, 116(2), pp. 205-219, (2004).
Dey et al., "Voruciclib, a clinical stage oral CDK9 inhibitor, represses MCL-1 and sensitizes high-risk Diffuse Large B-cell Lymphoma to BCL2 inhibition," Scientific Reports 7:18007, pp. 1-11, (2017).
Dorwald F.A., "Side Reactions in Organic Synthesis," Wiley: VCH, Weinheim, pp. IX of Preface pp. 1-15, (2005).
Huang, "Fluorescence polarization competition assay: the range of resolvable inhibitor potency is limited by the affinity of the fluorescent ligand," J. Biomol. Screen., 8(1), pp. 34-38, (2003).
Inoue-Yamauchi, Akane et al., "Targeting the differential addiction to anti-apoptotic bcl-2 family for cancer therapy," Nature Communications, vol. 8, (Jul. 2017), pp. 1-14.
International Search Report and Written Opinion for PCT/CN2019/096968, dated Oct. 22, 2019.
International Search Report and Written Opinion for PCT/CN2019/097028, dated Oct. 22, 2019.
International Search Report and Written Opinion for PCT/CN2019/097081, dated Oct. 29, 2019.
International Search Report and Written Opinion for PCT/CN2019/098252, dated Nov. 4, 2019.
International Search Report and Written Opinion for PCT/CN2019/120144, dated Feb. 24, 2020.
International Search Report for PCT/US2017/045428, dated Nov. 17, 2017.
Kirkin et al., "The role of Bcl-2 family members in tumorigenesis," Biochem. Biophys. Acta., 1644(2-3), pp. 229-249, (2004).
Kojima et al., "Concomitant Inhibition of MDM2 and Bcl-2 Protein Function Synergistically Induce Mitochondrial Apoptosis in AML," Cell Cycle, vol. 5, Iss. 23, pp. 2778-2786, (Dec. 2006).
Lehmann, Christian et al., "Superior anti-tumor activity of the MDM2 antagonist idasanutlin and the Bcl-2 inhibitor venetoclax in p53 wild-type acute myeloid Teukemia models," Journal of Hematology & Oncology, (2016), 9:50; pp. 1-13.
Metro, G. and Cappuzzo, Federico, "Emerging drugs for small-cell lung cancer," Expert Opin. Emerging Drugs, 14(4), pp. 591-606, (2009).
Moss, "Basic terminology of stereochemistry," Pure & Appl. Chem., 68(12), pp. 2193-2222, (1996).
Nakayama et al., "Targeted disruption of Bcl-2 alpha beta in mice: occurrence of gray hair, polycystic kidney disease, and lymphocytopenia," Proc. Natl. Acad. Sci. USA, 91(9), pp. 3700-3704, (1994).
Nikolovska-Coleska et al., "Development and optimization of a binding assay for the XIAP BIR3 domain using fluorescence polarization," Anal. Biochem., 332(2), pp. 261-273, (2004).
Pan et al., "Activation of p56 By Novel MDM2 Antagonist RG7388 Overcomes AML Inherent and Acguired Resistance to Bcl-2 Inhibitor ABT-199 (GDC-0199)," Blood, 124:2162; (2014).
Portell et al., "Abstract B40: Synergistic cytotoxicity of ibrutinib and the BCL2 antagonist ABT-199 in mantle cell lymphoma and chronic lymphocytic leukemia: Molecular analysis reveals mechanisms of target interactions," Hematologic Maliignancies, vol. 21, Issue 17, (Sep. 2015).
Reed et al., "BCL-2 family proteins: regulators of cell death involved in the pathogenesis of cancer and resistance to therapy," J. Cell Biochem., 60(1), pp. 23-32, (1996).
Reed, "Bcl-2 family proteins: strategies for overcoming chemoresistance in cancer," Adv. Pharmacol., 41, pp. 501-532, (1997).
Seymour et al., "Venetoclax plus rituximab in relapsed or refractory chronic Tymphocytic leukaemia: a phase 1b study," Lancet Onco. (Feb. 2017) 18(2), pp. 230-240.
Souers et al., "ABT-199, a potent and selective BCL-2 inhibitor, achieves antitumor activity while sparing platelets," Nat. Med., 19(2), pp. 202-208, (2013).
Tse et al., "ABT-263: a potent and orally bioavailable Bcl-2 family inhibitor," Cancer Res., 68(9), pp. 3421-3428, (2008).
Van Delft et al., "The BH3mimetic ABT-737 targets selective Bcl-2 proteins and efficiently induces apoptosis vai Bak/Bax if Mcl-1 is neutralized," Cancer Cell, 10(5), pp. 389-399, (2006).
Van Goethem et al., "Dual targeting of MDM2 and BCL2 as a therapeutic strategy in neuroblastoma," Oncotarget, vol. 8, No. 34, (2017), pp. 57047-57057.
Van Tonder et al., "Preparation and physicochemical characterization of 5 niclosamide solvates and 1 hemisolvate," AAPS PharmSciTech., 5(1), E12, (2004).
Venclexta, Venclexta tablets label, Translation (Dec. 14, 2017).
Venkatesh, J., "Role of the Development Scientist in Compound Lead Selection and Optimizatin" J. Pharm. Sci., vol. 89, No. 2, pp. 145-154, (2000).
Willis et al., "Apoptosis initiated when BH3 ligands engage multiple Bcl-2 homologs, not Bax or Bak," Science, 315(5813), pp. 856-859, (2007).
Written Opinion of the International Searching Authority for PCT/US2017/045428, dated Nov. 17, 2017.
Zelenetz et al., "Results of a Phase 1b Study of Venetoclax Plus R- or G- CHOP in Patients with B-Cell Non-Hodgkin Lymphoma," Blood, (Dec. 2016), vol. 128(22), pp. 3032-3035.
Zhang, "Apoptosis-based anticancer drugs," Nat. Rev. Drug Discov., 1(2), pp. 101-102, (2002).
Zinzani et al., "Phase 2 Study of Venetoclax Plus Rituximab or Randomized Ven Plus Bendamustine+Rituximab (BR) Versus BR in Patients ith Relapsed/Refractory Follicular Lymphoma: Interim Data," Blood, (Dec. 2016), vol. 128(22), pp. 617-620.
Enriqueta Felip, Mariacarmela Santarpia & Rafael Rosell, "Emerging drugs for non-small-cell lung cancer", Expert Opinion on Emerging Drugs, (2007) vol. 12, No. 3, pp. 449-460.

* cited by examiner

COMBINATION PRODUCT OF BCL-2 INHIBITOR AND CHEMOTHERAPEUTIC AGENT AND USE THEREOF IN THE PREVENTION AND/OR TREATMENT OF DISEASES

CROSS-REFERENCE TO RELATED APPLICATIONS

This application is a national phase application of PCT/CN2019/097081, filed Jul. 22, 2019, which application claims the benefit of and priority to Chinese Patent Application No. 201810862169.6, filed Jul. 31, 2018, the entire contents of each of which are incorporated by reference herein.

TECHNICAL FIELD

The invention belongs to the technical field of medicine, and in particular relates to a combination product comprising a Bcl-2 inhibitor and a chemotherapeutic agent and the use thereof in the prevention and/or treatment of diseases (for example, cancer).

BACKGROUND ART

Apoptosis (programmed cell death) is a natural pathway for the body to clear abnormal or unwanted cells, which can cause various diseases such as cancer if affected.

Anti-apoptotic Bcl-2 proteins are associated with many diseases. Bcl-2 family proteins are key regulators in the mitochondria-mediated apoptotic pathway. Escape from apoptosis is one of the characteristics of human cancer and is a common cause of clinical drug resistance.

With the advancement of molecular biology, molecular targeted therapy has become a hotspot in medical research (especially tumor research). The biological behavior of most tumors is not dominated by a single signaling pathway, but multiple signaling pathways. Thus, there is a need in the art for protocols and products for the combination of different target proteins and/or different signaling pathways that are capable of reducing the dose of single drug, reducing single drug side effects and/or acting in a synergistic manner for the purpose of preventing and/or treating diseases.

Contents of the Invention

In order to meet the needs in the prior art, the present invention provides a combination product comprising a Bcl-2 inhibitor and a chemotherapeutic agent and its use in the treatment and/or prevention of diseases (e.g., cancer).

In particular, a first aspect of the invention relates to a combination product comprising a Bcl-2 inhibitor and a chemotherapeutic agent.

In some embodiments, the Bcl-2 inhibitor is a compound of Formula I-A, or a pharmaceutically acceptable salt or solvate thereof:

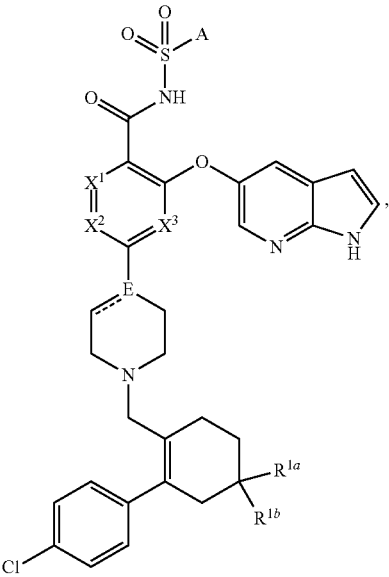

wherein:

A is

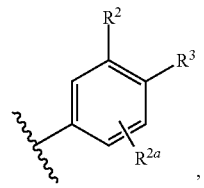

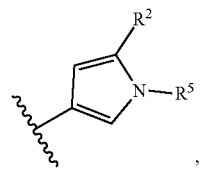

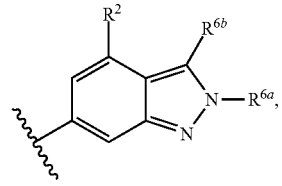

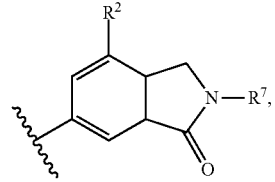

-continued

A-5
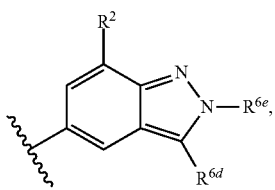

A-6
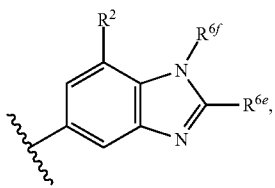

A-7
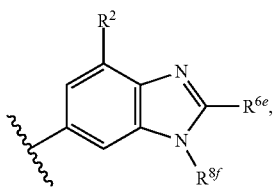

A-8
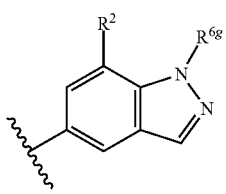

A-9
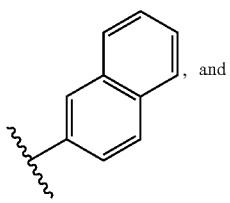, and

A-10
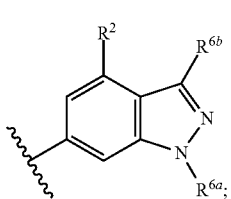

E is a carbon atom and ⹀ is a double bond; or

E is a —C(H)— and ⹀ is a single bond; or

E is a nitrogen atom and ⹀ is a single bond;

X1, X2 and X3 are each independently selected from the group consisting of —CR8═ and —N═;

R1a and R1b taken together with the carbon atom to which they are attached form a 3-, 4-, or 5-membered optionally substituted aliphatic ring; or R1a and R1b taken together with the carbon atom to which they are attached form a 4- or 5-membered optionally substituted heterocyclo;

R2 is selected from the group consisting of —NO2, —SO2CH3, and —SO2CF3;

R2a is selected from the group consisting of hydrogen and X;

R3 is selected from the group consisting of hydrogen, —CN, —C≡CH, and —N(R4a)(R4b);

R4a is selected from the group consisting of optionally substituted C1-6 alkyl, optionally substituted C3-6 cycloalkyl, heterocyclo, heteroalkyl, cycloalkylalkyl, and heterocycloalkyl;

R4b is selected from the group consisting of hydrogen and C1-4 alkyl;

R5 is selected from the group consisting of is selected from the group consisting of optionally substituted C1-6 alkyl, heterocyclo, cycloalkylalkyl, and heterocycloalkyl;

R6a, R6c, R6e, R6f, and R6g are each independently selected from the group consisting of hydrogen, optionally substituted C1-6 alkyl, optionally substituted C3-6 cycloalkyl, optionally substituted aryl, optionally substituted heteroaryl, heterocyclo, heteroalkyl, cycloalkylalkyl, and heterocycloalkyl;

R6b and R6d are each independently selected from the group consisting of hydrogen, C1-4 alkyl, and halogen;

R7 is selected from the group consisting of optionally substituted C1-6 alkyl, heterocyclo, heteroalkyl, cycloalkylalkyl, and heterocycloalkyl; and R8 is selected from the group consisting of hydrogen and halogen.

In some embodiments, the Bcl-2 inhibitor is selected from the group consisting of a compound or a pharmaceutically acceptable salt or solvate thereof:

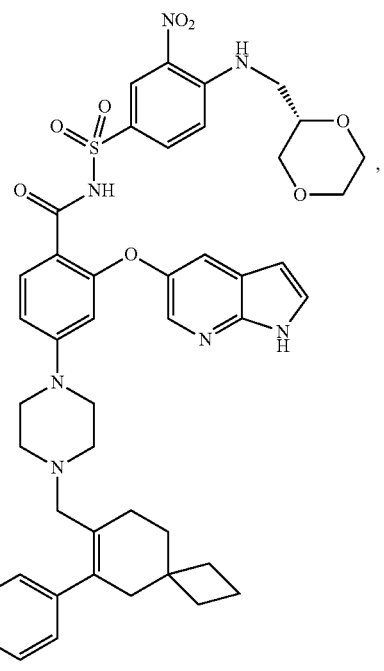

-continued

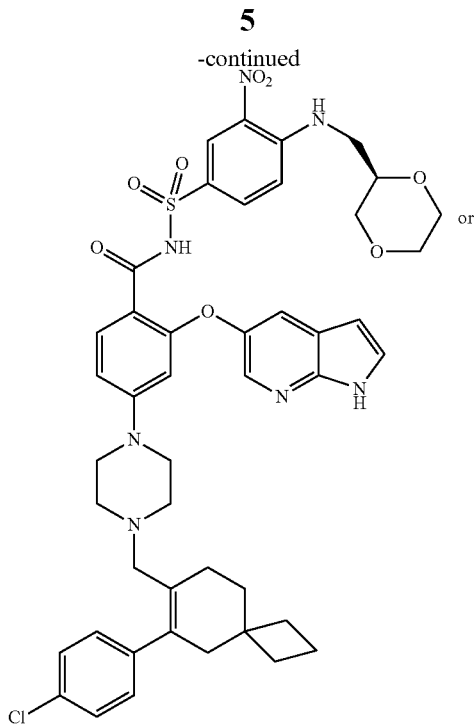 or

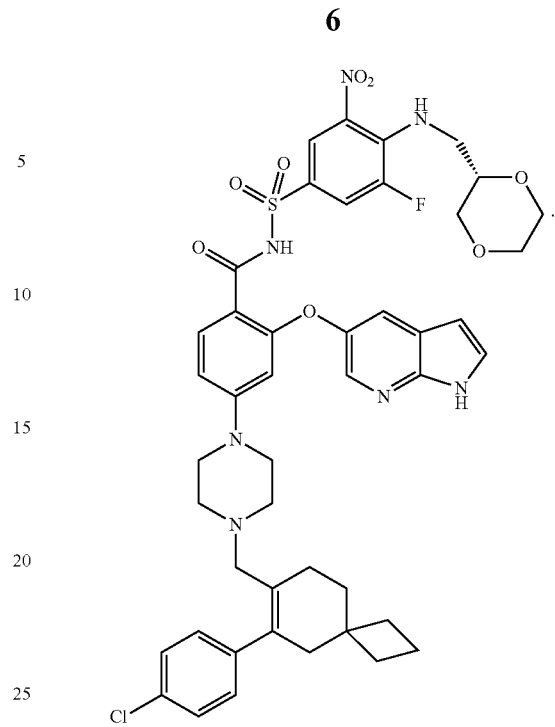

In some embodiments, the Bcl-2 inhibitor is the following compound or a pharmaceutically acceptable salt or solvate thereof:

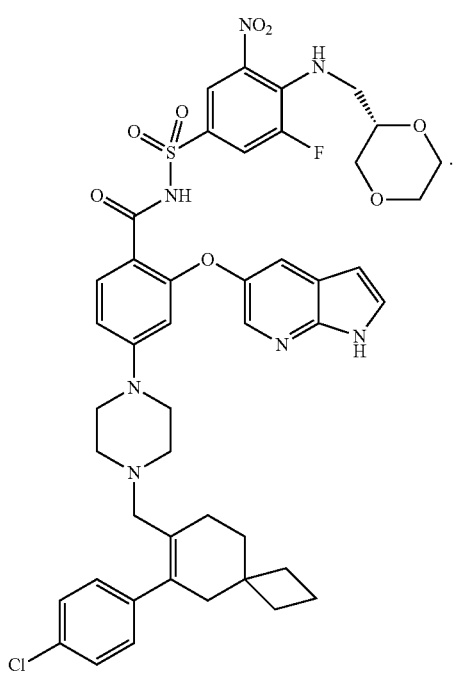 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

In some embodiments, the chemotherapeutic agent is selected from the group consisting of: actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, deoxyfluorouridine, doxorubicin, epirubicin, adriamycin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, thioguanine, topotecan, valrubicin, vemurafenib, vinblastine, vincristine, vindesine, vinorelbine, camptothecin or hydroxycamptothecin.

In some embodiments, the chemotherapeutic agent is topotecan.

In some embodiments, the combination product is in the form of a pharmaceutical composition.

In some embodiments, the Bcl-2 inhibitor and the chemotherapeutic agent are each in a separate preparation.

In some embodiments, the Bcl-2 inhibitor and the chemotherapeutic agent are administered simultaneously or sequentially.

In some embodiments, the combination product further comprises a pharmaceutically acceptable carrier, diluent or excipient.

In some embodiments, the combined product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor and a chemotherapeutic agent in the manufacture of a medicament for the prevention and/or treatment of a disease, in which the disease is cancer.

A third aspect of the invention relates to a combination product for preventing and/or treating a disease, in which the combination product comprises a Bcl-2 inhibitor and a chemotherapeutic agent, and the disease is cancer.

A fourth aspect of the invention relates to a method of preventing and/or treating a disease comprising administering a Bcl-2 inhibitor and a chemotherapeutic agent to a subject in need thereof, the disease is cancer.

In some embodiments, the cancer is selected from the group consisting of bladder cancer, breast cancer, cervical cancer, colon cancer (including colorectal cancer), esophageal cancer, head and neck cancer, liver cancer, lung cancer (small cell lung cancer and non-small cell lung cancer), melanoma, myeloma, neuroblastoma, ovarian cancer, pancreatic cancer, prostate cancer, kidney cancer, sarcoma (including osteosarcoma), skin cancer (including squamous cell cancer), gastric cancer, testicular cancer, thyroid cancer, uterine cancer, mesothelioma, cholangiocarcinoma, leiomyosarcoma, liposarcoma, melanoma, nasopharyngeal carcinoma, neuroendocrine carcinoma, ovarian cancer, renal cancer, salivary gland cancer, spindle cell cancer-induced metastases, non-Hodgkin's lymphoma, Hodgkin's lymphoma, acute myeloid leukemia (AML), acute lymphoblastic leukemia (ALL), diffuse large B-cell lymphoma (DLBCL), follicular Lymphoma (FL), chronic lymphocytic leukemia (CLL), chronic myelogenous leukemia (CML), mantle cell lymphoma (MCL).

In some embodiments, the cancer is small cell lung cancer (SCLC).

In some embodiments, the Bcl-2 inhibitor or a pharmaceutically acceptable salt or solvate thereof is administered in a dose from about 0.0025 to 1500 mg/day.

In some embodiments, the chemotherapeutic agent or a pharmaceutically acceptable salt or solvate thereof is administered in a dose from about 0.005 mg/day to about 1000 mg/day.

DETAILED DESCRIPTION OF THE INVENTION

Figure 1:
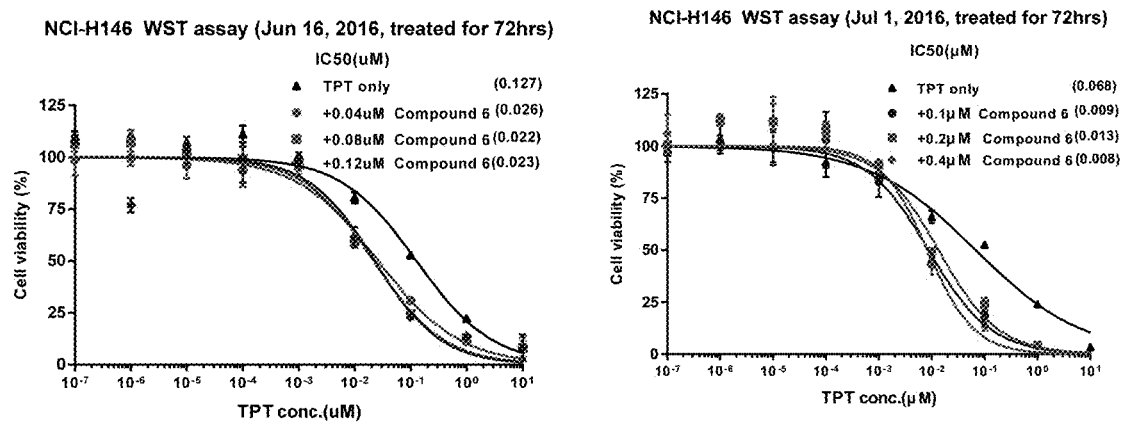
FIG. 1 shows the effect of Compound 6 in combination with the chemotherapeutic agent topotecan on tumor cells in NCI-H146 small cell lung cancer (SCLC).

A first aspect of the invention relates to a combination product comprising or consisting of a Bcl-2 inhibitor and a chemotherapeutic agent.

In some embodiments, the Bcl-2 inhibitor is a compound of Formula I-A, or a pharmaceutically acceptable salt or solvate thereof:

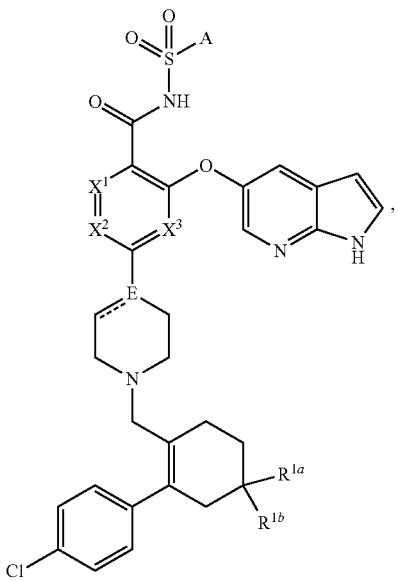

I-A wherein:
A is

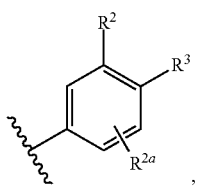

A-1

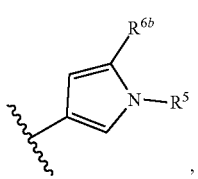

A-2

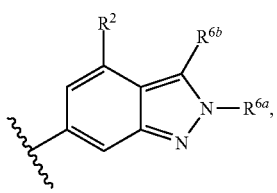

A-3

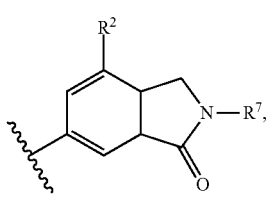

A-4

-continued

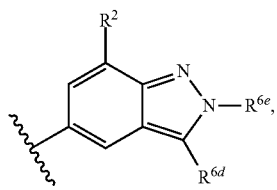
A-5

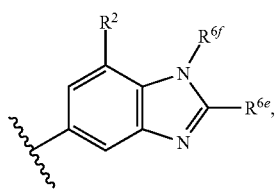
A-6

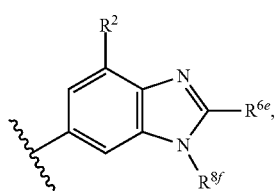
A-7

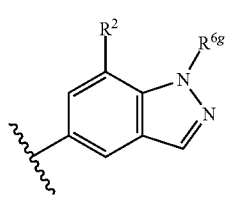
A-8

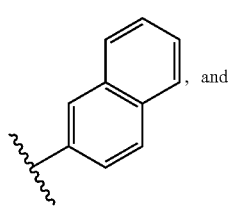
A-9, and

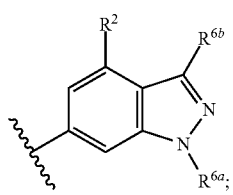
A-10

E is a carbon atom and ═ is a double bond; or
E is a —C(H)— and ═ is a single bond; or
E is a nitrogen atom and ═ is a single bond;
X1, X2 and X3 are each independently selected from the group consisting of —CR8═ and —N═;
R1a and R1b taken together with the carbon atom to which they are attached form a 3-, 4-, or 5-membered optionally substituted aliphatic ring; or
R1a and R1b taken together with the carbon atom to which they are attached form a 4- or 5-membered optionally substituted heterocyclo;
R2 is selected from the group consisting of —NO2, —SO2CH3, and —SO2CF3;
R2a is selected from the group consisting of hydrogen and X;
R3 is selected from the group consisting of hydrogen, —CN, —C≡CH, and —N(R4a)(R4b);

R4a is selected from the group consisting of optionally substituted C1-6 alkyl, optionally substituted C3-6 cycloalkyl, heterocyclo, heteroalkyl, cycloalkylalkyl, and heterocycloalkyl;
R4b is selected from the group consisting of hydrogen and C1-4 alkyl;
R5 is selected from the group consisting of optionally substituted C1-6 alkyl, heterocyclo, cycloalkylalkyl, and heterocycloalkyl;
R6a, R6c, R6e, R6f, and R6g are each independently selected from the group consisting of hydrogen, optionally substituted C1-6 alkyl, optionally substituted C3-6 cycloalkyl, optionally substituted aryl, optionally substituted heteroaryl, heterocyclo, heteroalkyl, cycloalkylalkyl, and heterocycloalkyl;
R6b and R6d are each independently selected from the group consisting of hydrogen, C1-4 alkyl, and halogen;
R7 is selected from the group consisting of optionally substituted C1-6 alkyl, heterocyclo, heteroalkyl, cycloalkylalkyl, and heterocycloalkyl; and
R8 is selected from the group consisting of hydrogen and halogen.

In the above compound of Formula I-A, the "X" in the definition of variant R2a refers to halogen. Further, halogen mentioned above refers to F, Cl, Br, or I.

In some embodiments, the Bcl-2 inhibitor is a compound of Formula I-A, wherein: A is selected from the group consisting of A-1, A-2, A-3, A-4, A-5, A-6, A-7, A-8, and A-9; R4a is selected from the group consisting of optionally substituted C1-6 alkyl, heterocyclo, heteroalkyl, cycloalkylalkyl, and heterocycloalkyl; and R6a, R6c, R6e, R6f and R6g are each independently selected from the group consisting of hydrogen, optionally substituted C1-6 alkyl, heterocyclo, heteroalkyl, cycloalkylalkyl, and heterocycloalkyl.

In some embodiments, the Bcl-2 inhibitor is a compound of Formula I, or a pharmaceutically acceptable salt or solvate thereof,

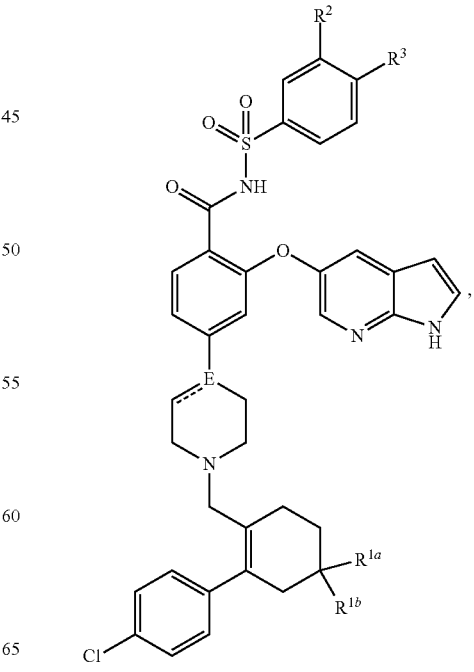
I wherein:

E is a carbon atom and ═ is a double bond; or E is —C(H)— and --- is a single bond; or E is a nitrogen atom and --- is a single bond;

R1a and R1b together with the carbon atom connected thereto form a 3-, 4-, or 5-membered optionally substituted aliphatic ring; or R1a and R1b together with the carbon atom connected thereto form a 4- or 5-membered optionally substituted heterocyclo;

R2 is selected from the group consisting of —NO2, —SO2CH3, and —SO2CF3;

R3 is selected from the group consisting of hydrogen, —CN, —C≡CH, and —N(R4a)(R4b);

R4a is selected from the group consisting of optionally substituted C1-6 alkyl, heterocyclo, cycloalkylalkyl, and heterocycloalkyl;

R4b is selected from the group consisting of hydrogen and C1-4 alkyl.

In some embodiments, the Bcl-2 inhibitor is a compound of Formula II, or a pharmaceutically acceptable salt or solvate thereof,

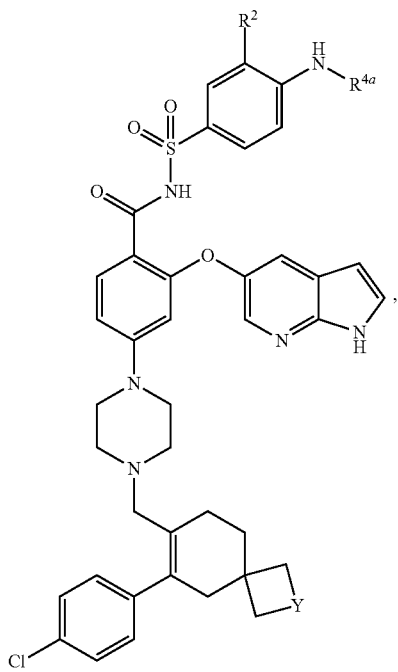

II wherein Y is selected from the group consisting of —CH2- and —O—, and R2 and R4a are as defined in connection with Formula I.

In some embodiments, the Bcl-2 inhibitor is a compound of Formula III, or a pharmaceutically acceptable salt or solvate thereof,

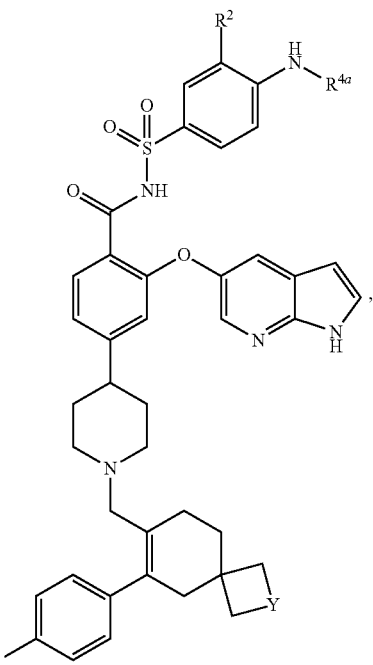

III wherein Y is selected from the group consisting of —CH2- and —O—, and R2 and R4a are as defined in connection with Formula I.

In some embodiments, the Bcl-2 inhibitor is a compound of Formula IV, or a pharmaceutically acceptable salt or solvate thereof,

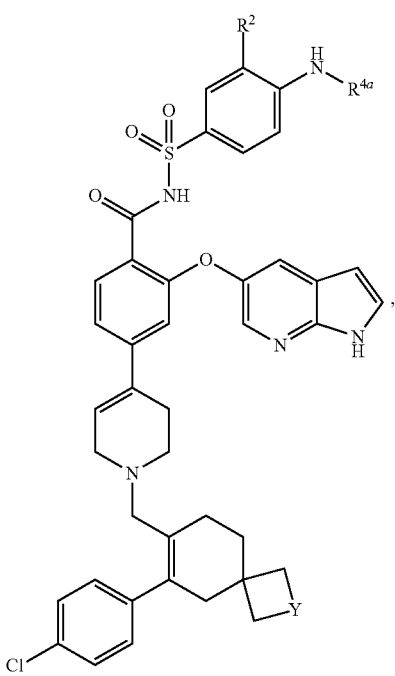

IV wherein Y is selected from the group consisting of —CH2- and —O—, and R2 and R4a are as defined in connection with Formula I.

In some embodiments, the Bcl-2 inhibitor is a compound of Formula V, or a pharmaceutically acceptable salt or solvate thereof,

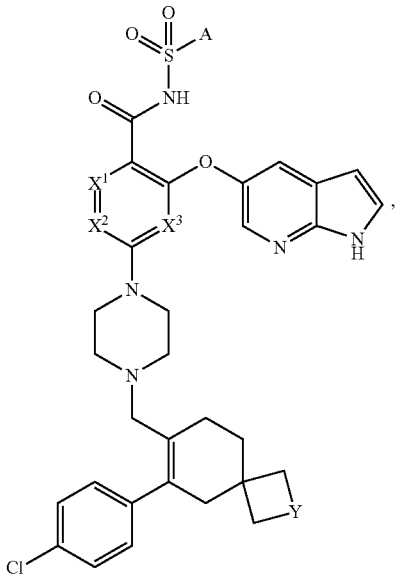

V wherein Y selected from the group consisting of —CH2— and —O—, and A, X1, X2, and X3 are as defined in connection with Formula I-A.

In some embodiments, the Bcl-2 inhibitor is a compound of Formula VI, or a pharmaceutically acceptable salt or solvate thereof,

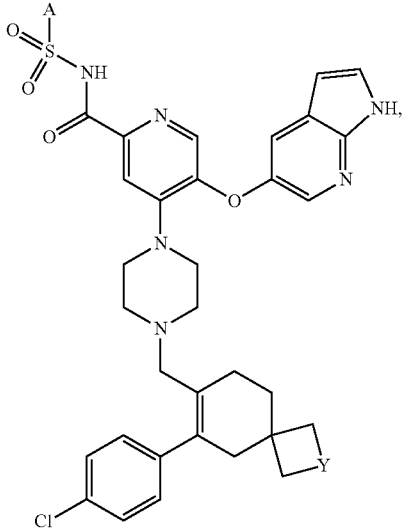

VI wherein Y selected from the group consisting of —CH2— and —O—, and A is as defined in connection with Formula I-A.

In some embodiments, the Bcl-2 inhibitor is a compound of Formula I-A, V or VI, or a pharmaceutically acceptable salt or solvate thereof, wherein A is A-1.

In some embodiments, the Bcl-2 inhibitor is a compound of Formula I-A, V or VI, or a pharmaceutically acceptable salt or solvate thereof, wherein A is A-2.

In some embodiments, the Bcl-2 inhibitor is a compound of Formula I-A, V or VI, or a pharmaceutically acceptable salt or solvate thereof, wherein A is A-3.

In some embodiments, the Bcl-2 inhibitor is a compound of Formula I-A, V or VI, or a pharmaceutically acceptable salt or solvate thereof, wherein A is A-4.

In some embodiments, the Bcl-2 inhibitor is a compound of Formula I-A, V or VI, or a pharmaceutically acceptable salt or solvate thereof, wherein A is A-5.

In some embodiments, the Bcl-2 inhibitor is a compound of Formula I-A, V or VI, or a pharmaceutically acceptable salt or solvate thereof, wherein A is A-6.

In some embodiments, the Bcl-2 inhibitor is a compound of Formula I-A, V or VI, or a pharmaceutically acceptable salt or solvate thereof, wherein A is A-7.

In some embodiments, the Bcl-2 inhibitor is a compound of Formula I-A, V or VI, or a pharmaceutically acceptable salt or solvate thereof, wherein A is A-8.

In some embodiments, the Bcl-2 inhibitor is a compound of Formula I-A, V or VI, or a pharmaceutically acceptable salt or solvate thereof, wherein A is A-9.

In some embodiments, the Bcl-2 inhibitor is a compound of Formula I-A, V or VI, or a pharmaceutically acceptable salt or solvate thereof, wherein A is A-10.

In some embodiments, the Bcl-2 inhibitor is a compound of Formula VII, or a pharmaceutically acceptable salt or solvate thereof,

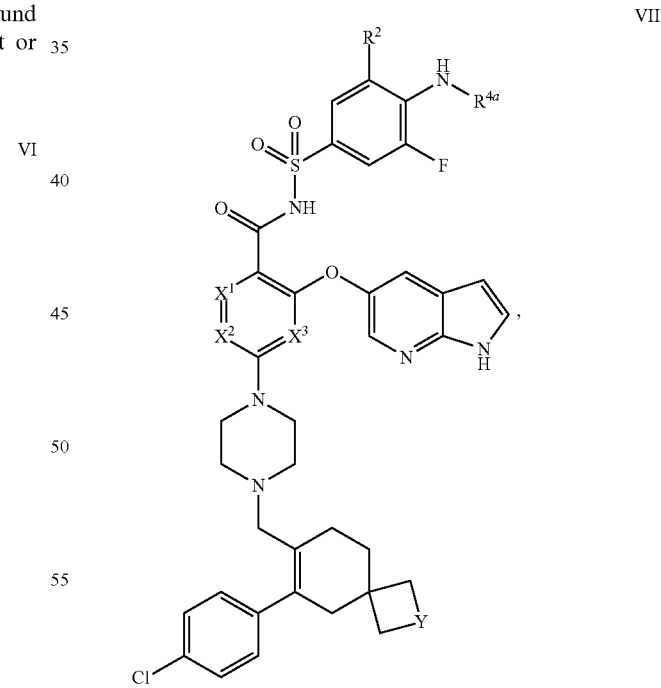

VII wherein Y selected from the group consisting of —CH2— and —O—, and X1, X2, X3, R2, and R4a are as defined in connection with Formula I-A.

In some embodiments, the Bcl-2 inhibitor is a compound of Formula I-A, V or VII, or a pharmaceutically acceptable salt or solvate thereof, wherein all X1, X2, and X3 are —CH=.

In some embodiments, the Bcl-2 inhibitor is a compound of Formula I-A, V or VII, or a pharmaceutically acceptable salt or solvate thereof, wherein X1 is —CF=, and both X2 and X3 are —CH=.

In some embodiments, the Bcl-2 inhibitor is a compound of Formula I-A, V or VII, or a pharmaceutically acceptable salt or solvate thereof, wherein both X1 and X3 are —CH=, and X2 is —CF=.

In some embodiments, the Bcl-2 inhibitor is a compound of Formula I-A, V or VII, or a pharmaceutically acceptable salt or solvate thereof, wherein both X1 and X2 are —CH=, and X3 is —CF=.

In some embodiments, the Bcl-2 inhibitor is a compound of Formula I-A, V or VII, or a pharmaceutically acceptable salt or solvate thereof, wherein X1 is —N=, and both X2 and X3 are —CH=.

In some embodiments, the Bcl-2 inhibitor is a compound of Formula I-A, V or VII, or a pharmaceutically acceptable salt or solvate thereof, wherein both X1 and X3 are —CH=, and X2 is —N=.

In some embodiments, the Bcl-2 inhibitor is a compound of Formula I-A, V or VII, or a pharmaceutically acceptable salt or solvate thereof, wherein both X1 and X2 are —CH=, and X3 is —N=.

In some embodiments, the Bcl-2 inhibitor is a compound of any one of Formulae II-VII, or a pharmaceutically acceptable salt or solvate thereof, wherein Y is —O—.

In some embodiments, the Bcl-2 inhibitor is a compound of any one of Formulae II-VII, or a pharmaceutically acceptable salt or solvate thereof, wherein Y is —CH2-.

In some embodiments, the Bcl-2 inhibitor is a compound of any one of Formulae I-A or I-VII, or a pharmaceutically acceptable salt or solvate thereof, wherein R2 is —NO2.

In some embodiments, the Bcl-2 inhibitor is a compound of any one of Formulae I-VI, or a pharmaceutically acceptable salt or solvate thereof, wherein R4a is selected from the group consisting of:

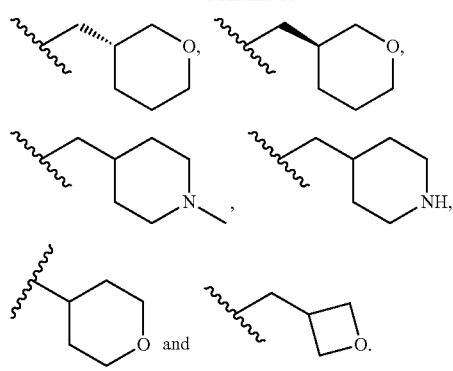

In some embodiments, the Bcl-2 inhibitor is a compound of any one of Formulae I-A or V-VII, or a pharmaceutically acceptable salt or solvate thereof, wherein R4a, R5, R6a, and R7 are each independently selected from the group consisting of:

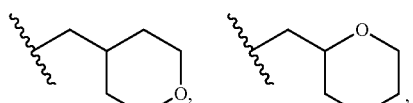
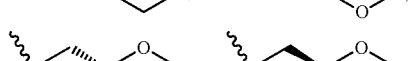
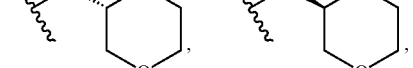
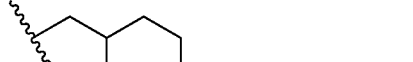
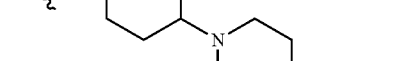
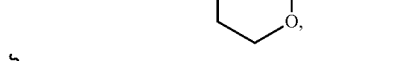
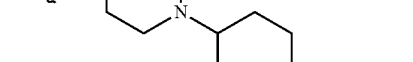
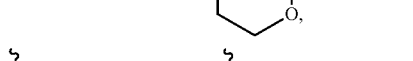
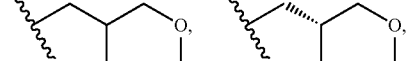
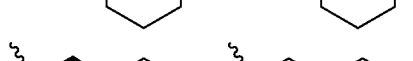
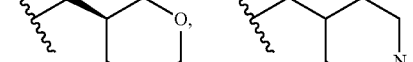
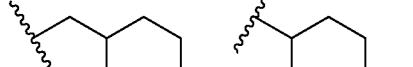
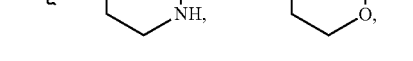

In some embodiments, the Bcl-2 inhibitor is a compound of Formula VIII, or a pharmaceutically acceptable salt or solvate thereof, wherein R2a is hydrogen or fluoro and R4a is as defined in connection with Formula I-A.

VIII

In some embodiments, the Bcl-2 inhibitor is a compound of Formula VIII, or a pharmaceutically acceptable salt or solvate thereof, wherein R4a is selected from the group consisting of:

In some embodiments, the Bcl-2 inhibitor is a compound selected from one or more of the compounds of Table 1, or a pharmaceutically acceptable salt or solvate thereof.

TABLE 1

| Cpd. No. | Structure | Name |
|---|---|---|
| 1 | 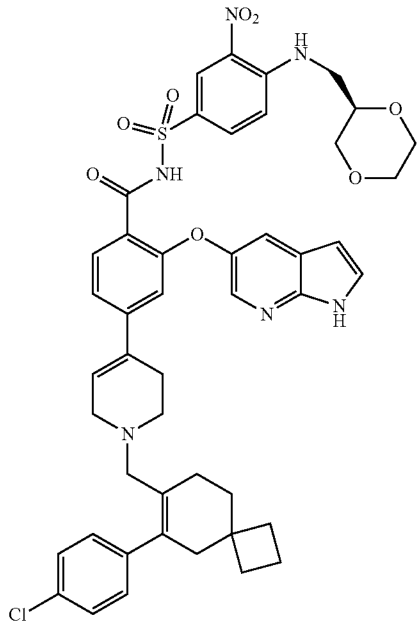 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide |
| 2 | 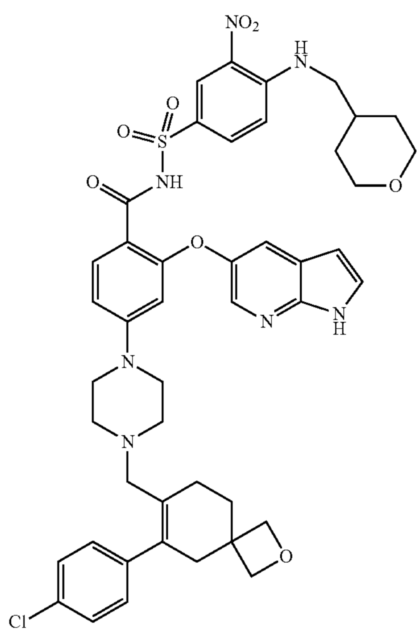 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide |

TABLE 1-continued
| Cpd. No. | Structure | Name |
|---|---|---|
| 3 | 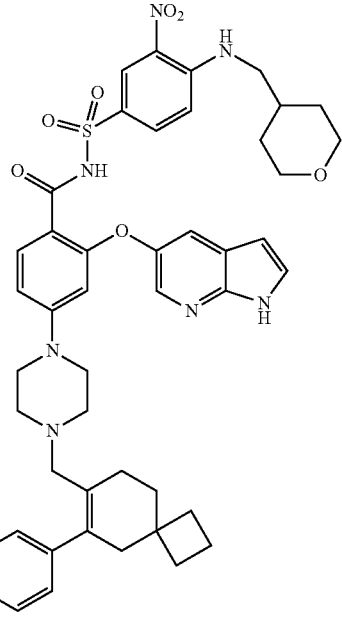 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 4 | 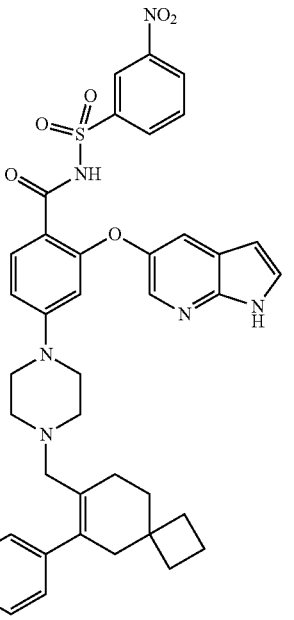 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitrophenyl)sulfonyl)benzamide |

TABLE 1-continued

| Cpd. No. | Structure | Name |
|---|---|---|
| 5 | 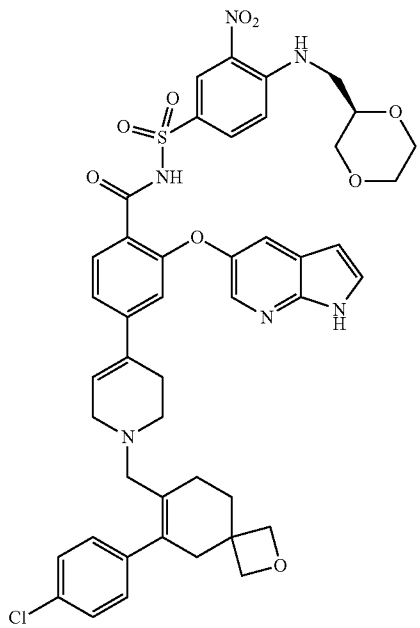 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide |
| 6 | 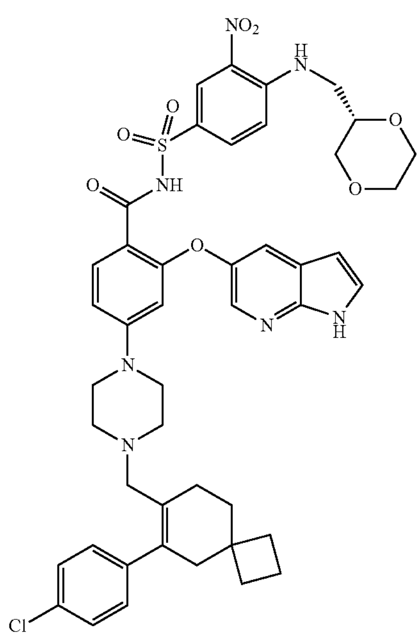 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-continued

| Cpd. No. | Structure | Name |
|---|---|---|
| 7 | 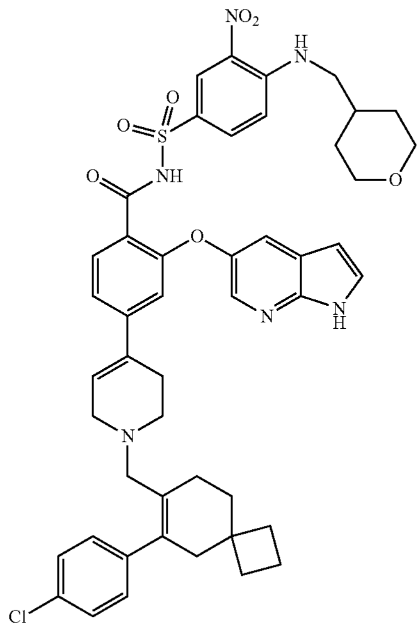 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 8 | 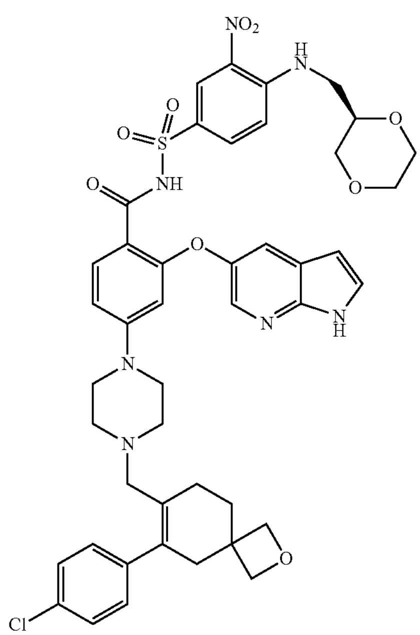 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide |

TABLE 1-continued
| Cpd. No. | Structure | Name |
|---|---|---|
| 9 | 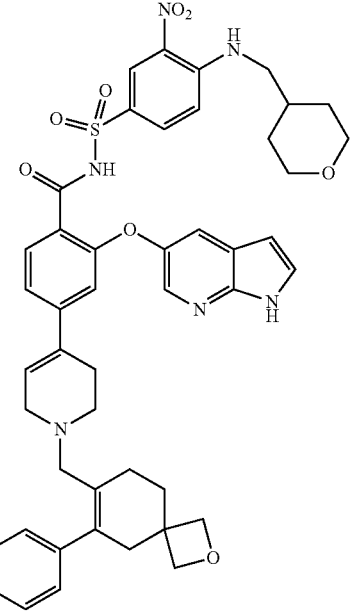 | 2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 10 | 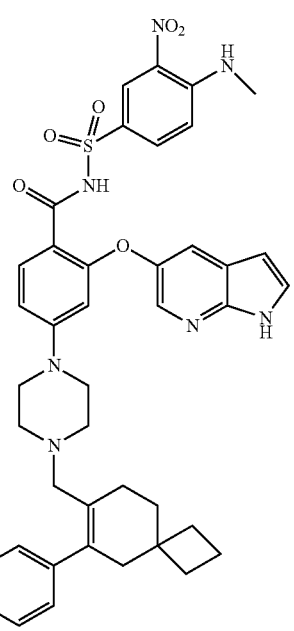 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(methylamino)-3-nitrophenyl)sulfonyl)benzamide |

TABLE 1-continued

| Cpd. No. | Structure | Name |
|---|---|---|
| 11 | 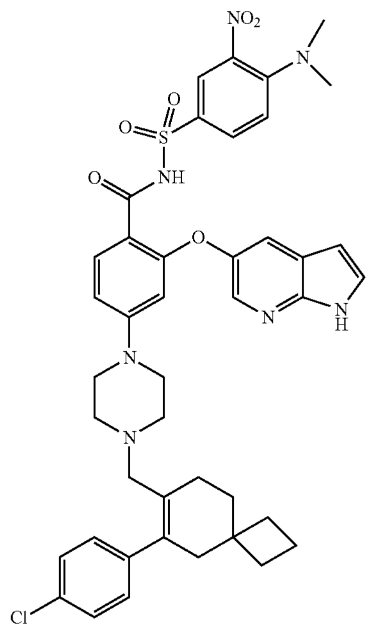 [SMILES: CN(C)c1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(dimethylamino)-3-nitrophenyl)sulfonyl)benzamide |
| 12 | 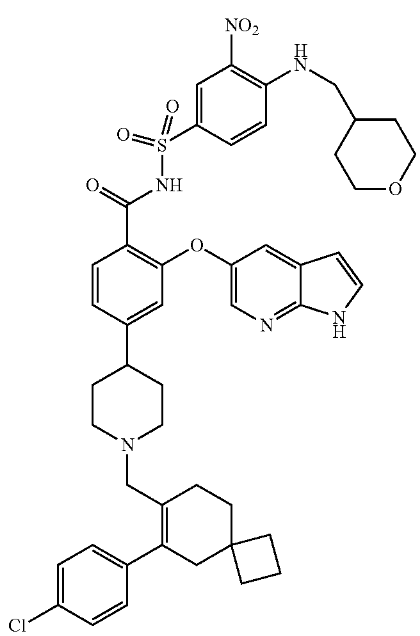 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide |

TABLE 1-continued
| Cpd. No. | Structure | Name |
|---|---|---|
| 13 | 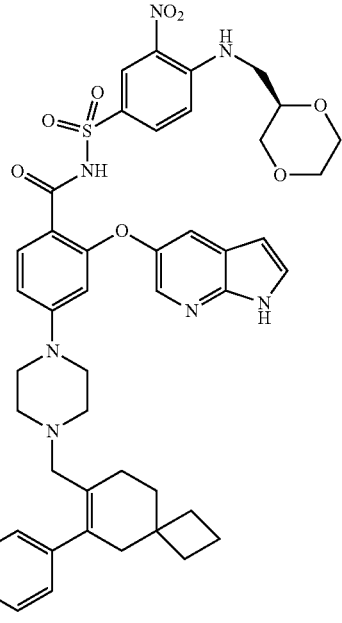 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 14 | 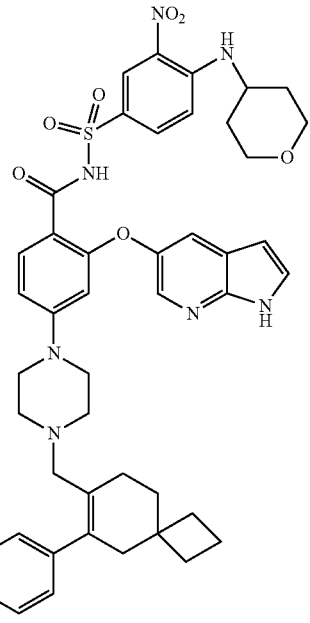 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((tetrahydro-2H-pyran-4-yl)amino)phenyl)sulfonyl)benzamide |

TABLE 1-continued
| Cpd. No. | Structure | Name |
|---|---|---|
| 15 | 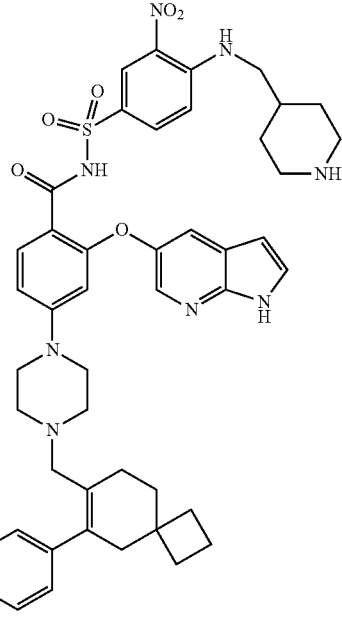 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((piperidin-4-ylmethyl)amino)phenyl)sulfonyl)benzamide |
| 16 | 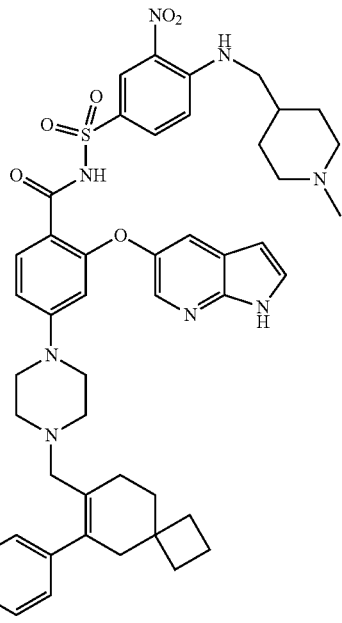 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(((1-methylpiperidin-4-yl)methyl)amino)-3-nitrophenyl)sulfonyl)benzamide |

TABLE 1-continued
| Cpd. No. | Structure | Name |
|---|---|---|
| 17 | 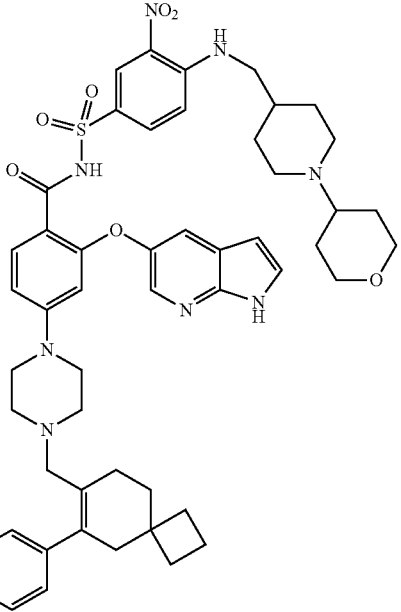 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(tetrahydro-2H-pyran-4-yl)piperidin-4-yl)methyl)amino)phenyl)sulfonyl)benzamide |
| 18 | 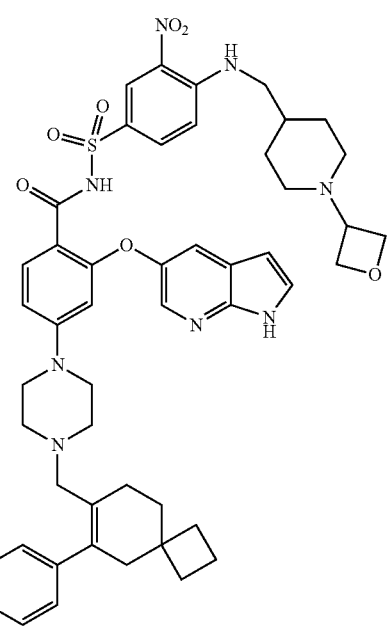 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(oxetan-3-yl)piperidin-4-yl)methyl)amino)phenyl)sulfonyl)benzamide |

TABLE 1-continued

| Cpd. No. | Structure | Name |
| --- | --- | --- |
| 19 | 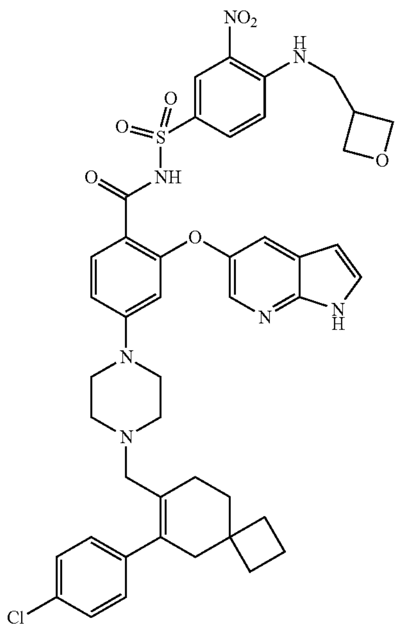 [SMILES: O=C(NS(=O)(=O)c1ccc(NCC2COC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((oxetan-3-ylmethyl)amino)phenyl)sulfonyl)benzamide |
| 20 | 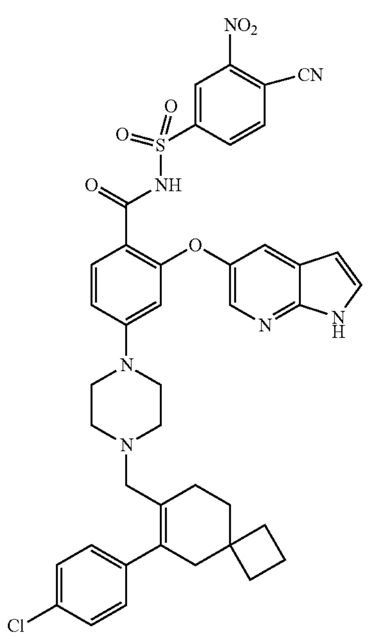 [SMILES: N#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-cyano-3-nitrophenyl)sulfonyl)benzamide |

TABLE 1-continued

| Cpd. No. | Structure | Name |
|---|---|---|
| 21 | 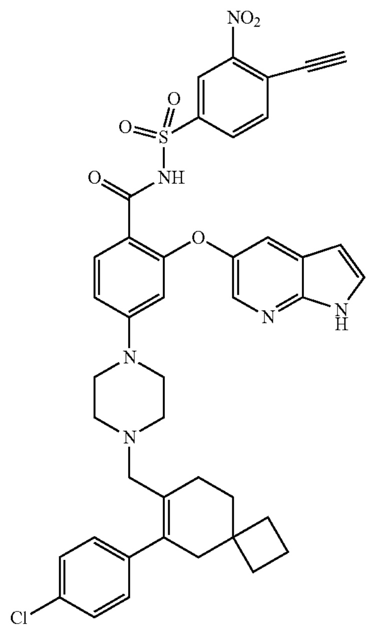 [SMILES: C#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-ethynyl-3-nitrophenyl)sulfonyl)benzamide |

In some embodiments, the Bcl-2 inhibitor is a compound selected from one or more of the compounds of Table 1-A, or a pharmaceutically acceptable salt or solvate thereof.

TABLE 1-A

| Cpd. No. | Structure | Name |
|---|---|---|
| 22 | 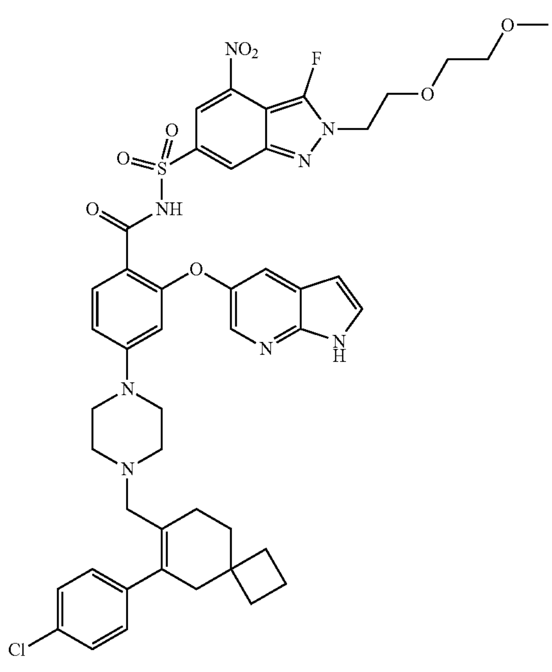 [SMILES: COCCOCCn1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2c1F] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-2-(2-(2-methoxyethoxy)ethyl)-4-nitro-2H-indazol-6-yl)sulfonyl)benzamide |

TABLE 1-A-continued

| Cpd. No. | Structure | Name |
|---|---|---|
| 23 | 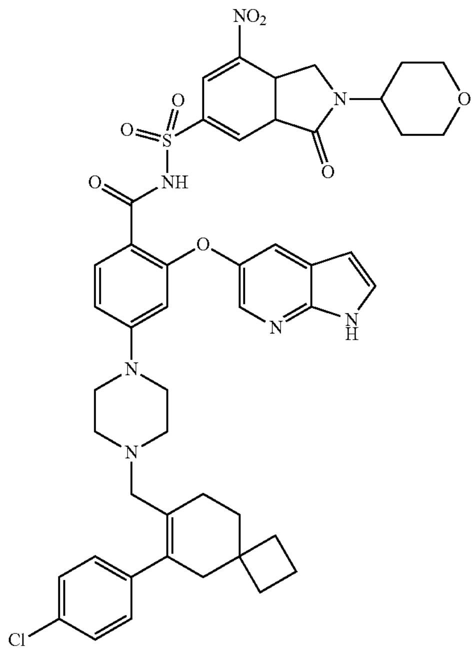 [SMILES: O=C(NS(=O)(=O)C1=CC2C(=O)N(C3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-(tetrahydro-2H-pyran-4-yl)-2,3,3a,7a-tetrahydro-1H-isoindol-5-yl)sulfonyl)benzamide |
| 24 | 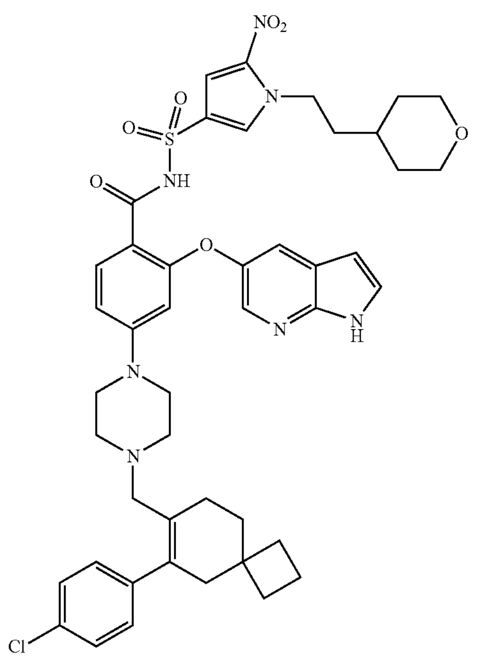 [SMILES: O=C(NS(=O)(=O)c1cc([N+](=O)[O-])n(CCC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-(2-(tetrahydro-2H-pyran-4-yl)ethyl)-1H-pyrrol-3-yl)sulfonyl)benzamide |

TABLE 1-A-continued

| Cpd. No. | Structure | Name |
|---|---|---|
| 25 | 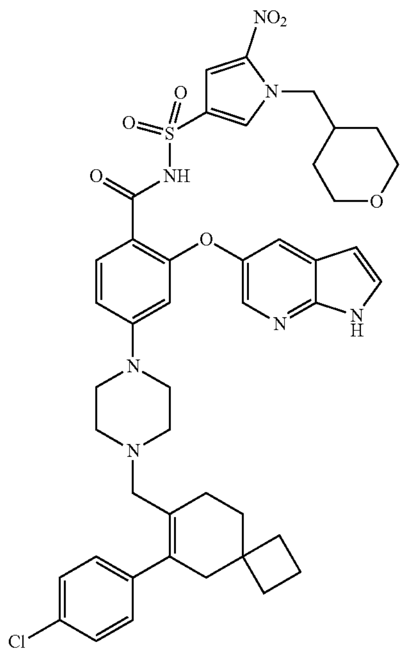 [SMILES: O=C(NS(=O)(=O)c1cc([N+](=O)[O-])n(CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-((tetrahydro-2H-pyran-4-yl)methyl)-1H-pyrrol-3-yl)sulfonyl)benzamide |
| 26 | 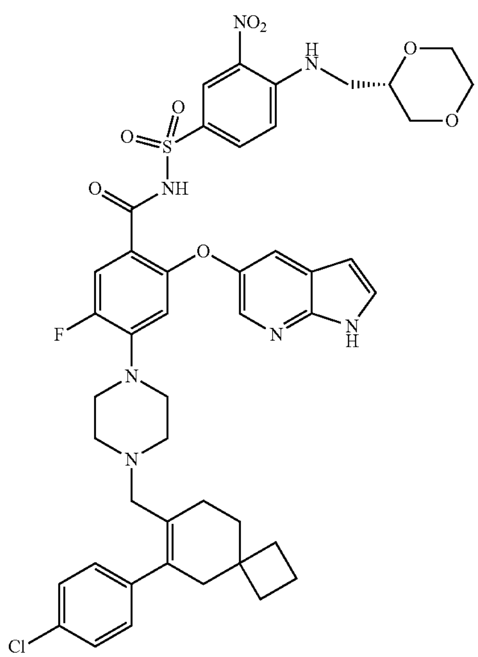 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |

TABLE 1-A-continued

| Cpd. No. | Structure | Name |
|---|---|---|
| 27 | 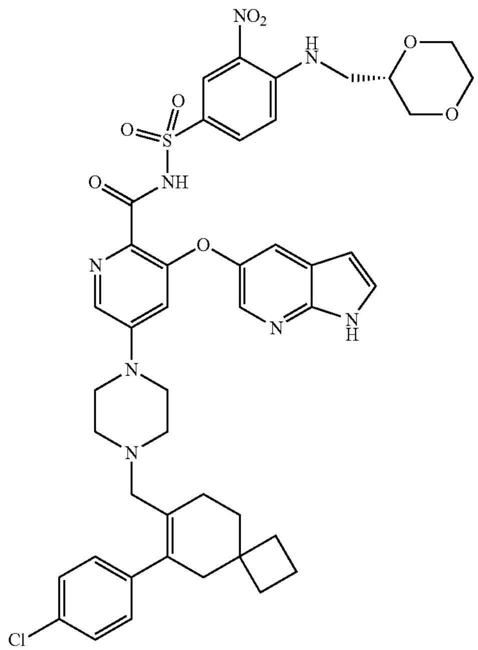 [SMILES: O=C(NS(=O)(=O)c1ccc(NC[C@H]2COCCO2)c([N+](=O)[O-])c1)c1ncc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-3-((1H-pyrrolo[2,3-b]pyridin-5-yl)oxy)-5-(4-((6-(4-chlorophenyl)spiro[3.5]non-6-en-7-yl)methyl)piperazin-1-yl)picolinamide |
| 28 | 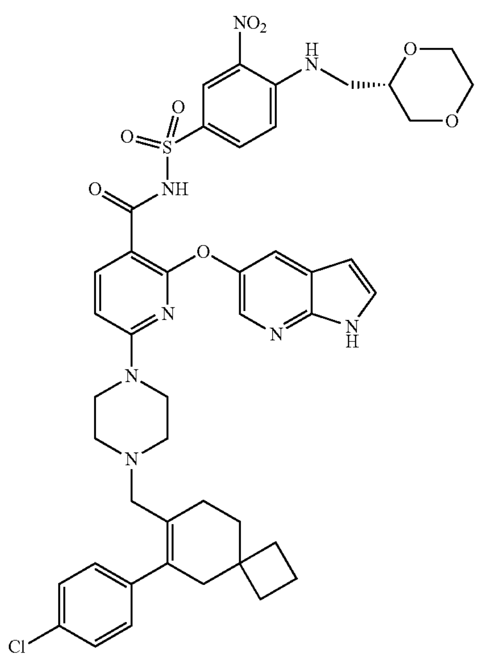 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)nc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-6-(4-((6-(4-chlorophenyl)spiro[3.5]non-6-en-7-yl)methyl)piperazin-1-yl)nicotinamide |

TABLE 1-A-continued
| Cpd. No. | Structure | Name |
|---|---|---|
| 29 | 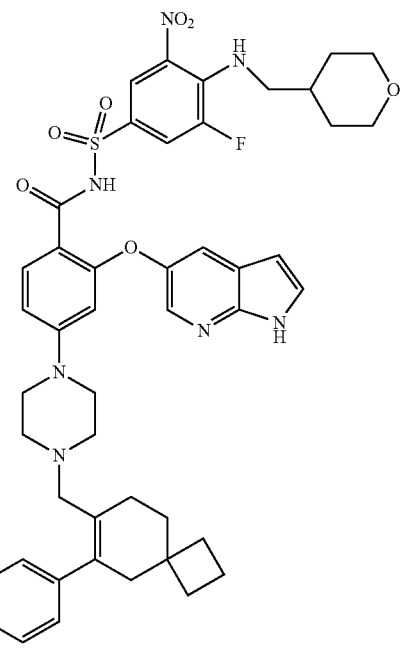 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-5-nitro-4-(((tetrahydro-2H-pyran-4-yl)methyl)amino)phenyl)sulfonyl)benzamide |
| 30 | 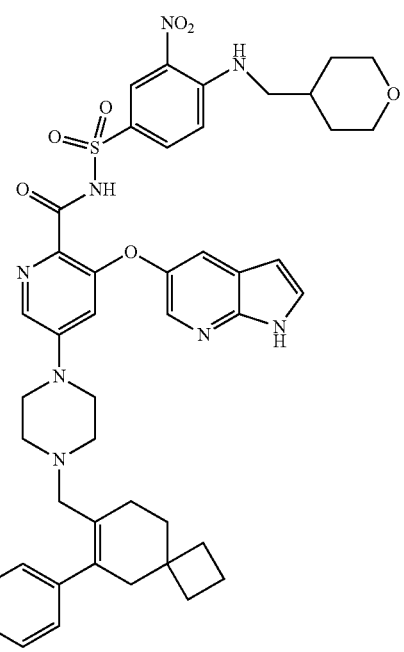 | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)picolinamide |

TABLE 1-A-continued

| Cpd. No. | Structure | Name |
|---|---|---|
| 31 | 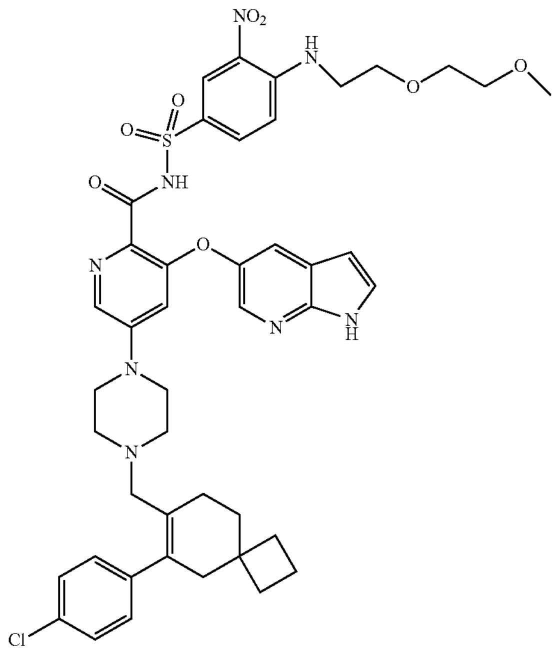 [SMILES: COCCOCCNc1ccc(S(=O)(=O)NC(=O)c2ncc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |
| 32 | 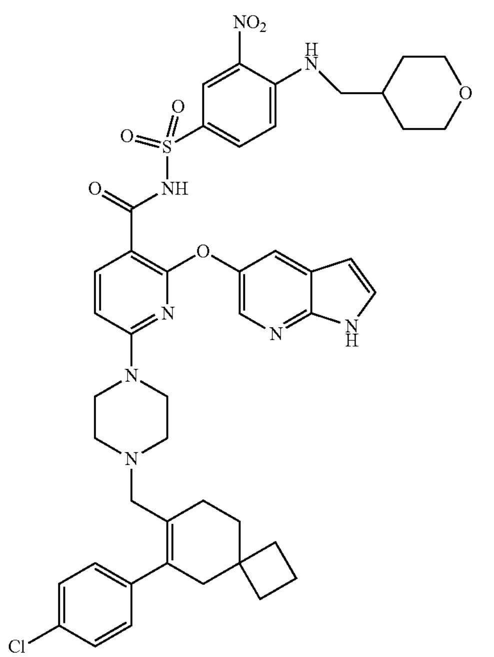 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)nc1Oc1cnc2[nH]ccc2c1] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)nicotinamide |

TABLE 1-A-continued

| Cpd. No. | Structure | Name |
|---|---|---|
| 33 | 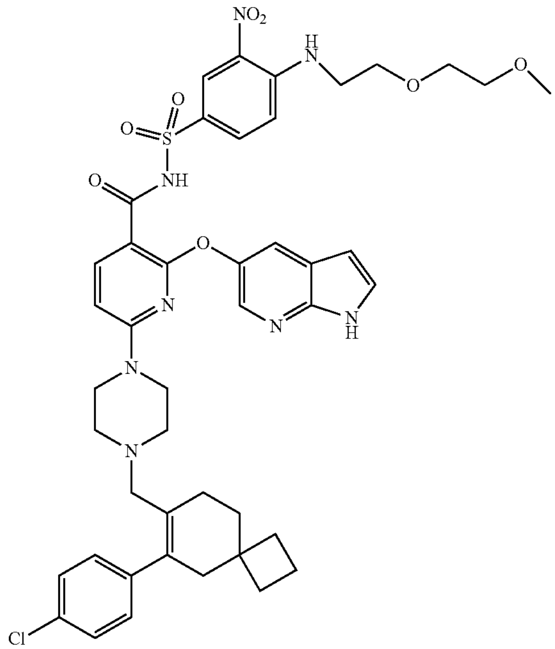 [SMILES: COCCOCCNc1ccc(S(=O)(=O)NC(=O)c2ccc(N3CCN(CC4=C(c5ccc(Cl)cc5)CC5(CCC5)CC4)CC3)nc2Oc2cnc3[nH]ccc3c2)cc1[N+](=O)[O-]] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)nicotinamide |
| 34 | 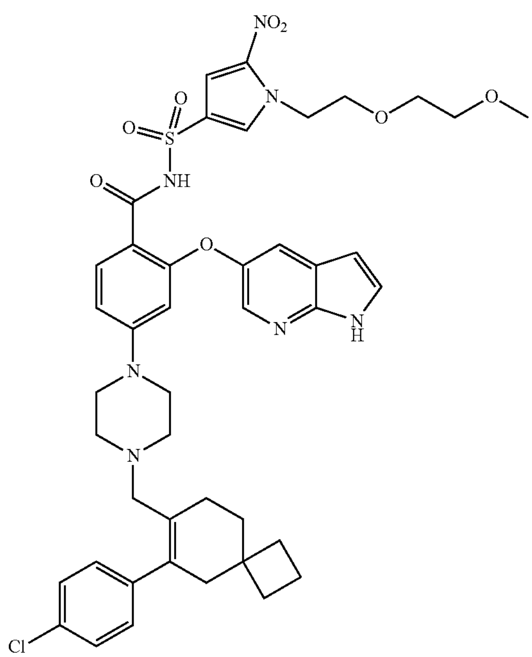 [SMILES: COCCOCCn1cc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |

TABLE 1-A-continued
| Cpd. No. | Structure | Name |
|---|---|---|
| 35 | 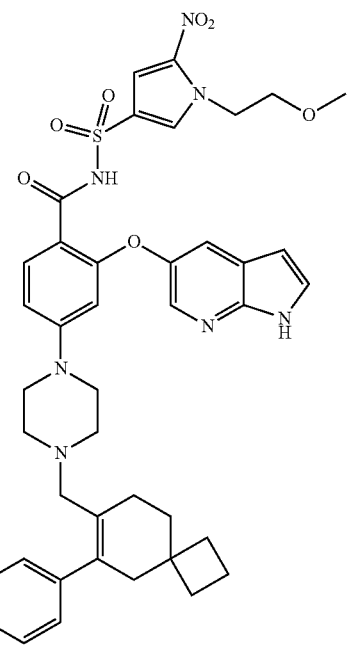 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-(2-methoxyethyl)-5-nitro-1H-pyrrol-3-yl)sulfonyl)benzamide |
| 36 | 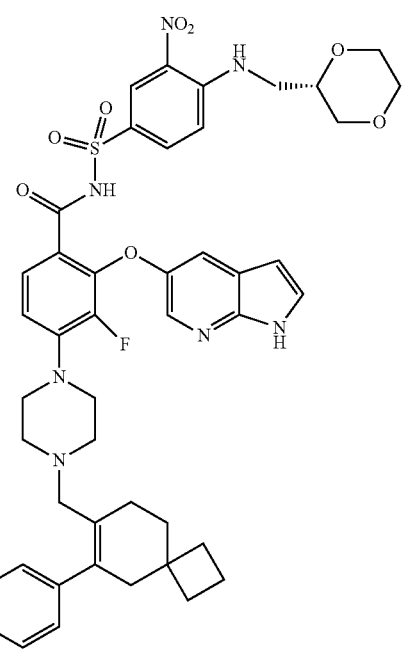 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluorobenzamide |

TABLE 1-A-continued
| Cpd. No. | Structure | Name |
|---|---|---|
| 37 | 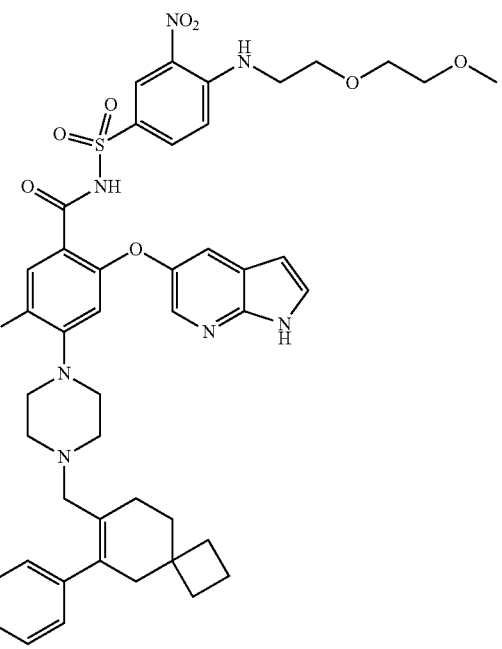 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluoro-N-((4-((2-(2-methoxyethoxy)ethyl)amino)-3-nitrophenyl)sulfonyl)benzamide |
| 38 | 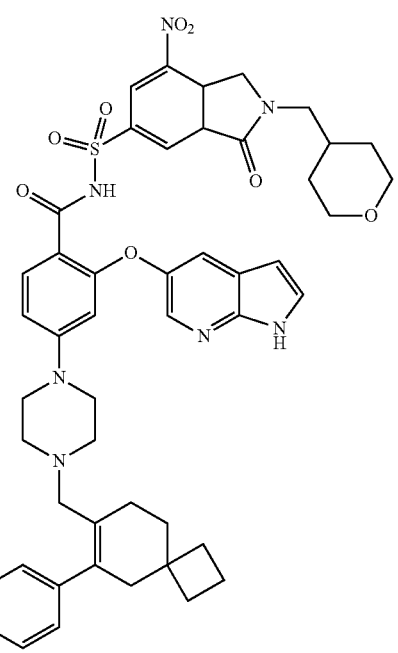 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-((tetrahydro-2H-pyran-4-yl)methyl)-2,3,3a,7a-tetrahydro-1H-isoindol-5-yl)sulfonyl)benzamide |

TABLE 1-A-continued
| Cpd. No. | Structure | Name |
|---|---|---|
| 39 | 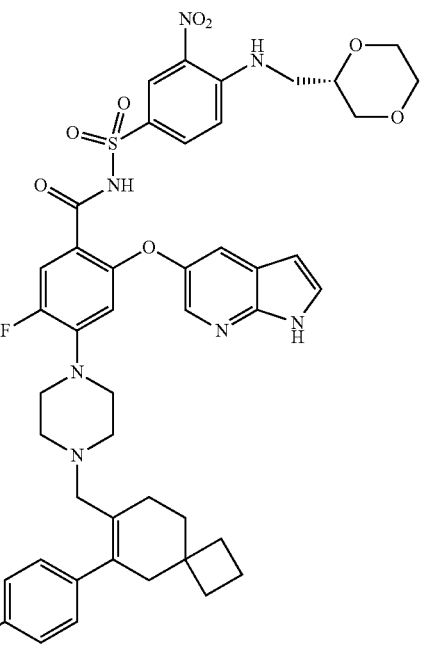 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |
| 40 | 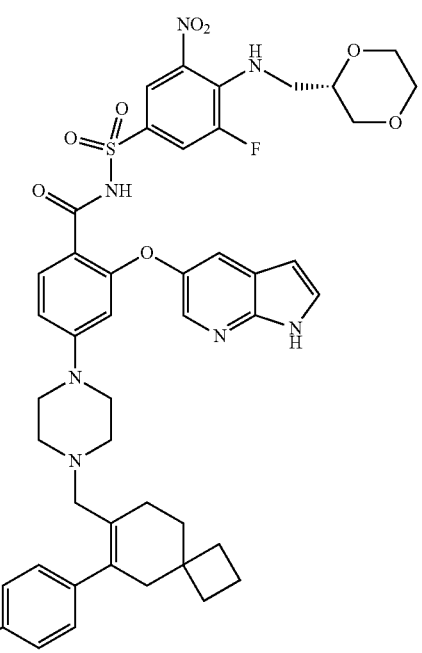 | (S)-N-((4-(((1,4-dioxan-2-yl)methyl)amino)-3-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued
| Cpd. No. | Structure | Name |
|---|---|---|
| 41 | 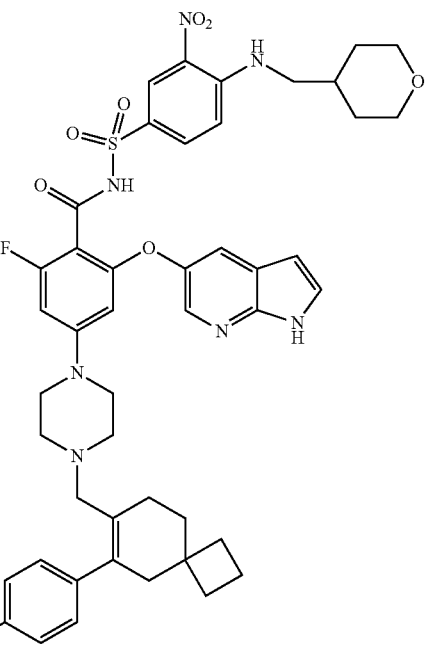 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-6-fluoro-N-((3-nitro-4-(((tetrahydro-2H-pyran-4-yl)methyl)amino)phenyl)sulfonyl)benzamide |
| 42 | 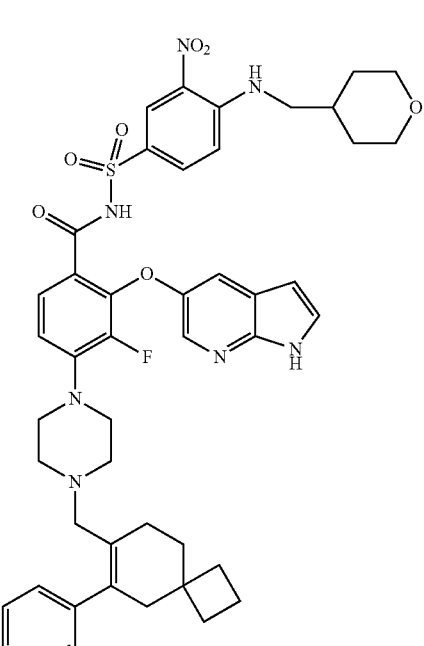 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((3-nitro-4-(((tetrahydro-2H-pyran-4-yl)methyl)amino)phenyl)sulfonyl)benzamide |

TABLE 1-A-continued
| Cpd. No. | Structure | Name |
|---|---|---|
| 43 | 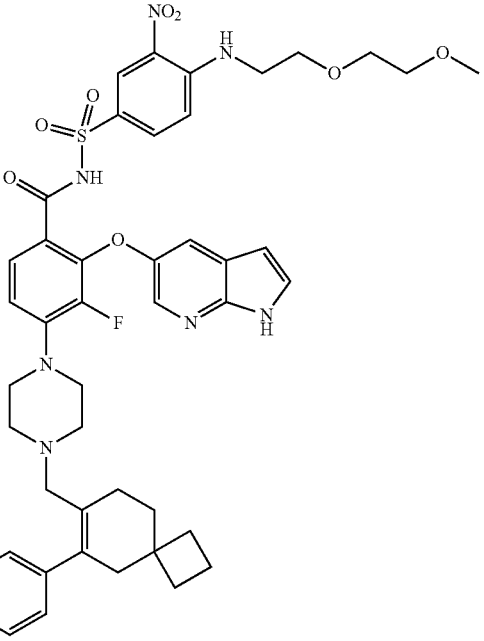 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((4-((2-(2-methoxyethoxy)ethyl)amino)-3-nitrophenyl)sulfonyl)benzamide |
| 44 | 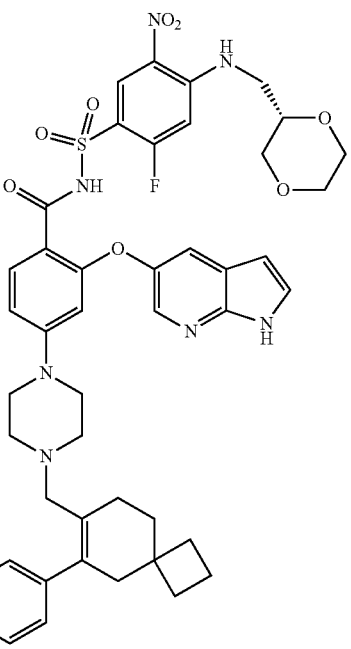 | (S)-N-((4-(((1,4-dioxan-2-yl)methyl)amino)-2-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

| Cpd. No. | Structure | Name |
| --- | --- | --- |
| 45 | 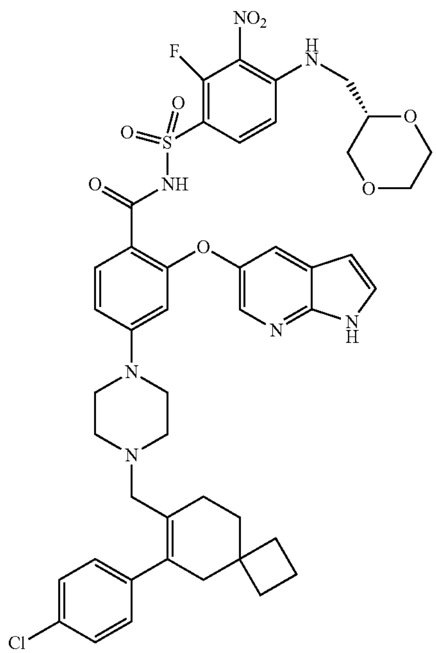 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-3-nitrophenyl)sulfonyl)-24(1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 46 | 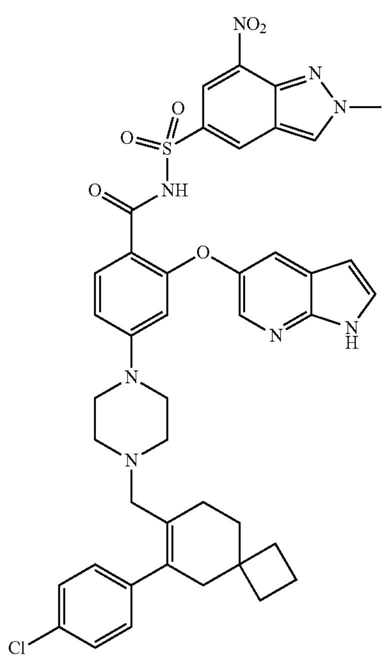 [SMILES: Cn1cc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-methyl-7-nitro-2H-indazol-5-yl)sulfonyl)benzamide |

TABLE 1-A-continued

| Cpd. No. | Structure | Name |
|---|---|---|
| 47 | 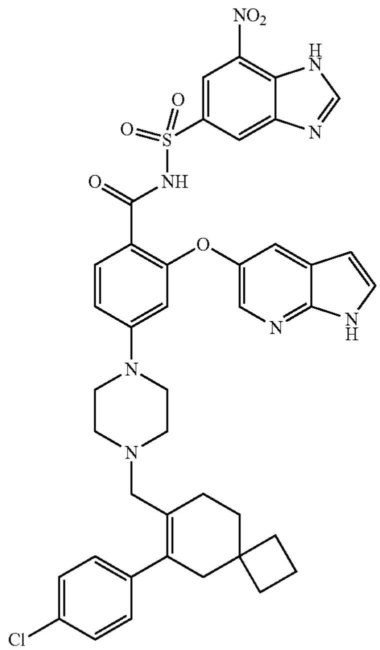 [SMILES: O=C(NS(=O)(=O)c1cc([N+](=O)[O-])c2[nH]cnc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1H-benzo[d]imidazol-5-yl)sulfonyl)benzamide |
| 48 | 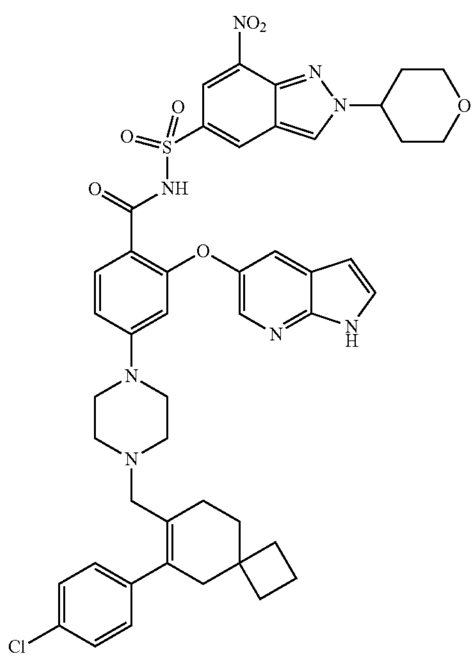 [SMILES: O=C(NS(=O)(=O)c1cc([N+](=O)[O-])c2nn(C3CCOCC3)cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(tetrahydro-2H-pyran-4-yl)-2H-indazol-5-yl)sulfonyl)benzamide |

TABLE 1-A-continued
| Cpd. No. | Structure | Name |
|---|---|---|
| 49 | 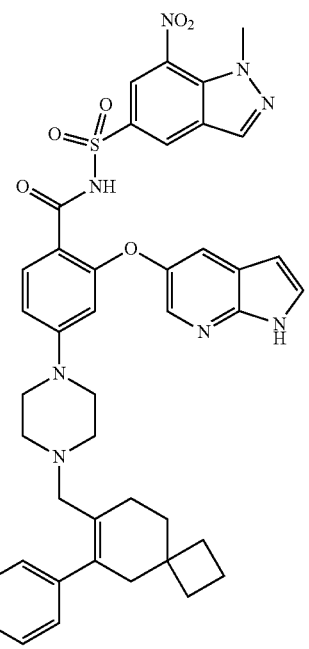 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-7-nitro-1H-indazol-5-yl)sulfonyl)benzamide |
| 50 | 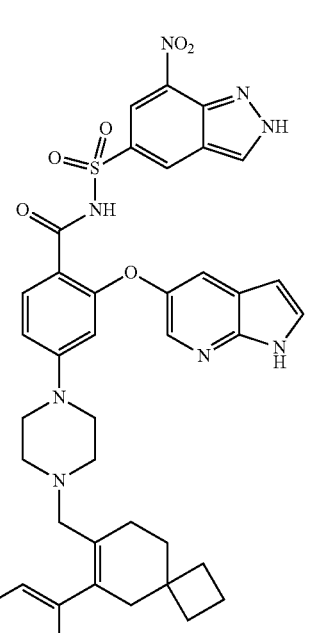 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2H-indazol-5-yl)sulfonyl)benzamide |

TABLE 1-A-continued

| Cpd. No. | Structure | Name |
|---|---|---|
| 51 | 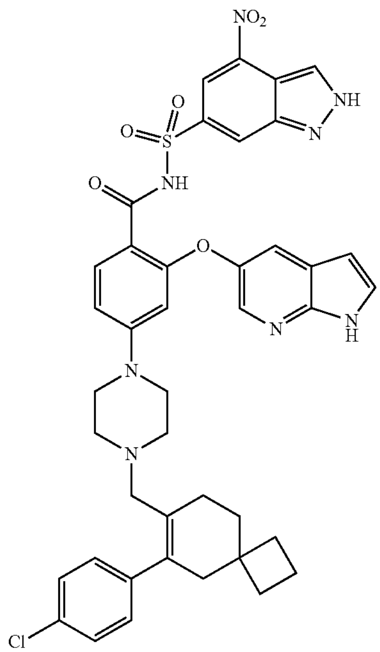 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2H-indazol-6-yl)sulfonyl)benzamide |
| 52 | 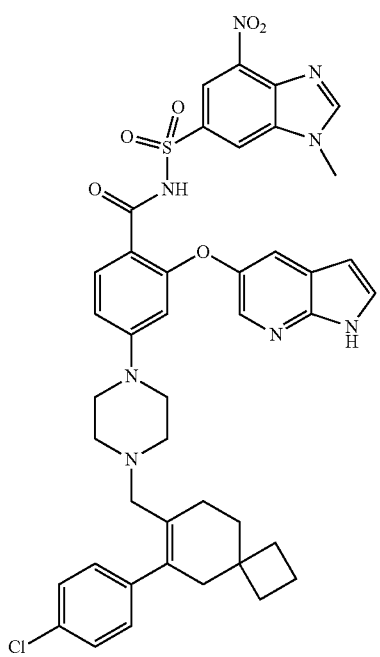 [SMILES: Cn1cnc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-4-nitro-1H-benzo[d]imidazol-6-yl)sulfonyl)benzamide |

TABLE 1-A-continued
| Cpd. No. | Structure | Name |
|---|---|---|
| 53 | 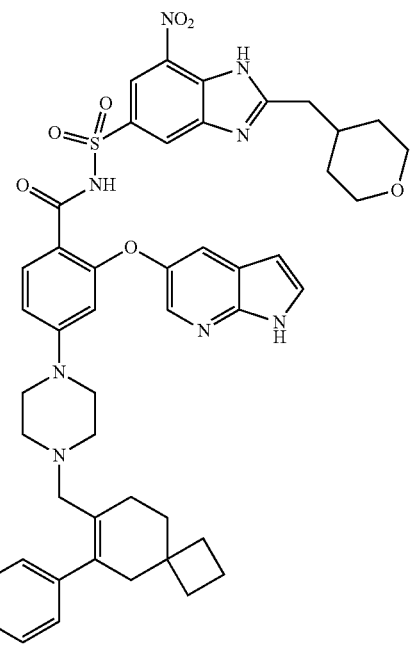 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-1H-benzo[d]imidazol-5-yl)sulfonyl)benzamide |
| 54 | 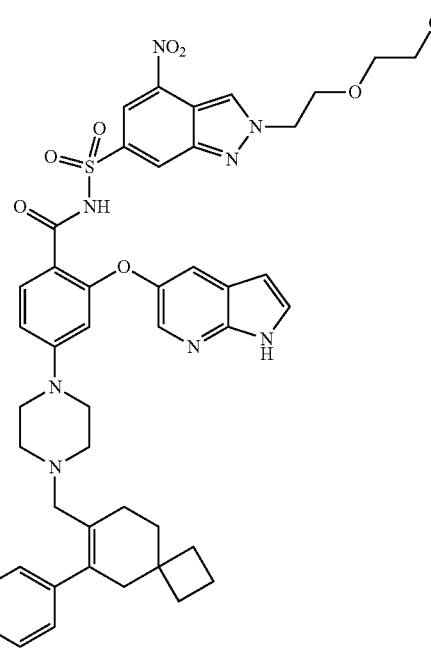 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-(2-methoxyethoxy)ethyl)-4-nitro-2H-indazol-6-yl)sulfonyl)benzamide |

TABLE 1-A-continued

| Cpd. No. | Structure | Name |
|---|---|---|
| 55 | 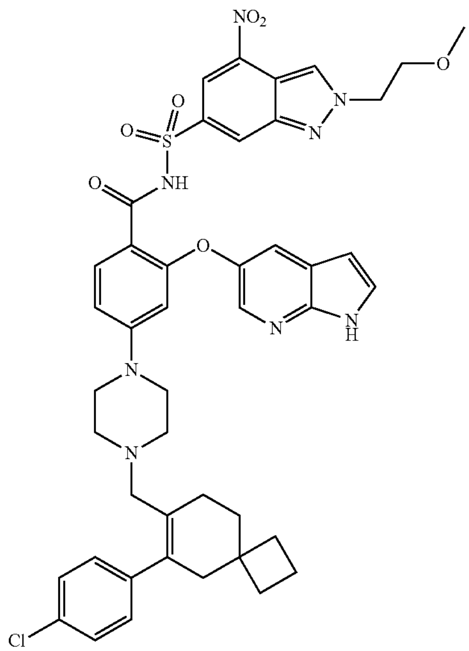 [SMILES: COCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-methoxyethyl)-4-nitro-2H-indazol-6-yl)sulfonyl)benzamide |
| 56 | 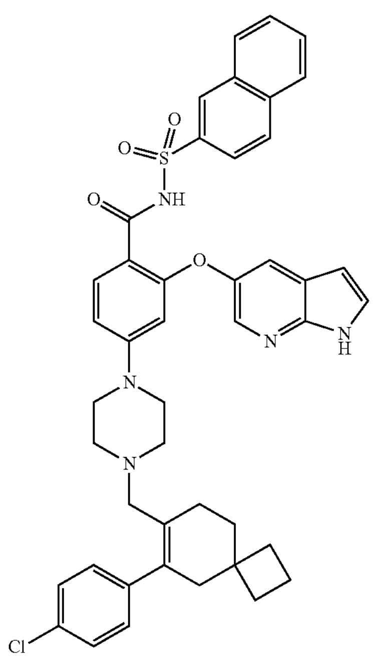 [SMILES: O=C(NS(=O)(=O)c1ccc2ccccc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-(naphthalen-2-ylsulfonyl)benzamide |

In some embodiments, the Bcl-2 inhibitor is the compound of Table 1-B, or a pharmaceutically acceptable salt or solvate thereof.

TABLE 1-B

| Cpd. No. | Structure | Name |
|---|---|---|
| 57 | 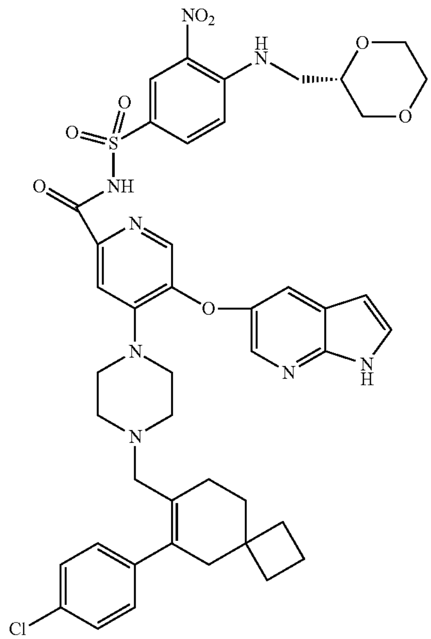 [SMILES: O=C(NS(=O)(=O)c1ccc(NC[C@H]2COCCO2)c([N+](=O)[O-])c1)c1cc(N2CCN(CC3=C(c4ccc(Cl)cc4)CC4(CCC4)CC3)CC2)c(Oc2cnc3[nH]ccc3c2)cn1] | (S)-N-((4-(((1,4-dioxan-2-yl)methyl)amino)-3-nitrophenyl)sulfonyl)-5-((1H-pyrrolo[2,3-b]pyridin-5-yl)oxy)-4-(4-((6-(4-chlorophenyl)spiro[3.5]non-6-en-7-yl)methyl)piperazin-1-yl)picolinamide |

In some embodiments, the combination product is in the form of a pharmaceutical composition.

In some embodiments, the Bcl-2 inhibitor and the chemotherapeutic agent are each in a separate preparation.

In some embodiments, the Bcl-2 inhibitor and the chemotherapeutic agent are administered simultaneously or sequentially.

In some embodiments, the Bcl-2 inhibitor and the chemotherapeutic agent may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the combination product of the invention comprising the Bcl-2 inhibitor and the chemotherapeutic agent in the form of a pharmaceutical composition (preferably, each in a separate dosage unit form), as desired, can be daily administered for, including but not limited to: 1 time, 2 times, 3 times, 4 times, 5 times or 6 times.

In some embodiments, the combination product of the invention comprising the Bcl-2 inhibitor and the chemotherapeutic agent in the form of a pharmaceutical composition (preferably, in the form of a dosage unit), as desired, can be daily administered for, including but not limited to: 1 time, 2 times, 3 times, 4 times, 5 times or 6 times.

In some embodiments, the combination product can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor, or a pharmaceutically acceptable salt or solvate thereof, is administered in an amount from about 0.0025 to 1500 mg/day. The amount of the Bcl-2 inhibitor is 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 460 mg, 470 mg, 480 mg, 487 mg, 490 mg, 500 mg, 550 mg, 600 mg, 650 mg, 700 mg, 750 mg, 800 mg, 850 mg, 900 mg, 950 mg, 1000 mg, and a range between the respective amounts, for example, 1 mg to 1000 mg, 30 mg to 900 mg, 30 mg to 800 mg, 30 mg to 900 mg, 30 mg to 800 mg, 30 mg to 700 mg, 30 mg to 600 mg, 30 mg to 500 mg, 30 mg to 490 mg, 30 mg to 487 mg, etc.; and the chemotherapeutic agent or a pharmaceutically acceptable salt or solvate thereof is administered in an amount from about 0.005 mg/day to about 5000 mg/day. The amount of the chemotherapeutic agent, such as the amount of topotecan, is 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 4.1 mg, 4.2 mg, 4.3 mg, 4.4 mg, 4.5 mg, 4.6 mg, 4.7 mg, 4.8 mg, 4.88 mg, 4.9 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, and a range between the respective amounts, for example, 0.1 mg to 1000 mg, 0.5 mg to 1000 mg, 1 mg to 1000 mg, 4.88 mg to 1000 mg, 4.88 mg to 900 mg, 4.88 mg to 800 mg, 4.88 mg to 700 mg, 4.88 mg to 600 mg, 4.88 mg to 500 mg, 4.88 mg to 400 mg, 4.88 mg to 300 mg, 4.88 mg to 200 mg, 4.88 mg to 100 mg, 4.88 mg to 50 mg, 4.88 mg to 10 mg, etc.

In some embodiments, the combination product further comprises a pharmaceutically acceptable carrier, diluent or excipient.

In some embodiments, the combination product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor and a chemotherapeutic agent in the manufacture of a medicament for the prevention and/or treatment of a disease selected from the group consisting of cancer.

In some embodiments, the Bcl-2 inhibitor is a compound (e.g, Compound I-A), or a pharmaceutically acceptable salt or solvate thereof, as specifically described in the first aspect of the invention.

In some embodiments, the medicament is in the form of a pharmaceutical composition.

In some embodiments, the Bcl-2 inhibitor and the chemotherapeutic agent are each in a separate preparation.

In some embodiments, the Bcl-2 inhibitor and the chemotherapeutic agent are administered simultaneously or sequentially.

In some embodiments, the Bcl-2 inhibitor and the chemotherapeutic agent may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the medicament of the invention comprising the Bcl-2 inhibitor and the chemotherapeutic agent in the form of a pharmaceutical composition (preferably, each in a separate dosage unit form), as desired, can be daily administered for, including but not limited to: 1 time, 2 times, 3 times, 4 times, 5 times or 6 times.

In some embodiments, the medicament of the invention comprising the Bcl-2 inhibitor and the chemotherapeutic agent in the form of a pharmaceutical composition (preferably, in the form of a dosage unit), as desired, can be daily administered for, including but not limited to: 1 time, 2 times, 3 times, 4 times, 5 times or 6 times.

In some embodiments, the medicament can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or a pharmaceutically acceptable salt or solvate thereof, and the MDM2 inhibitor or a pharmaceutically acceptable salt or solvate thereof, are administered in a daily amount as described above in the first aspect of the invention in the detailed description of the invention.

Further, the cancer described in the present invention includes, but is not limited to, a cancer selected from the group consisting of: adrenal cancer, lymphoid epithelioma, acinic cell carcinoma, lymphoma, acoustic neuroma, acute lymphocytic leukemia, acral lentiginous melanoma, acute myelogeous leukemia, acrospiroma, chronic lymphocytic leukemia, acute eosinophilic leukemia, liver cancer, acute erythroid leukemia, small cell lung cancer, acute lymphoblastic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, adenocarcinoma, malignant triton tumor, adenoid cystic carcinoma, mantle cell lymphoma, adenoma, marginal zone B cell lymphoma, adenomatoid odontogenic tumor, mast cell leukemia, adenosquamous carcinoma, mediastinal germ cell tumor, adipose tissue neoplasm, medullary carcinoma of the breast, adrenal cortical carcinoma, medullary thyroid carcinoma, adult T-cell leukemia/lymphoma, medulloblastoma, aggressive NK cell leukemia, melanoma, AIDS-related lymphoma, meningiomas, alveolar rhabdomyosarcoma, merkel cell carcinoma, alveolar soft tissue sarcoma, mesothelioma, ameloblastic fibroma, metastatic urothelial carcinoma, anaplastic large cell lymphoma, mixed mullerian tumor, anaplastic thyroid cancer, mucinous tumor, angioimmunoblastic T-cell lymphoma, multiple myeloma, angiomyolipoma, muscle tissue neoplasm, angiosarcoma, mycosis fungoides, astrocytoma, myxoid liposarcoma, atypical malformation rhabdoid tumor, myxoma, B cell chronic lymphocytic leukemia, myxosarcoma, B-cell prolymphocytic leukemia, nasopharyngeal carcinoma, B-cell lymphoma, neurinoma, basal cell carcinoma, neuroblastoma, biliary tract cancer, neurofibromatosis, bladder cancer, neuroma, blastoma, nodular melanoma, bone cancer, ocular cancer, Brenner tumor, oligodendroma, brown tumor, oligodendroglioma, Burkitt's lymphoma, oncocytoma, breast cancer, optic nerve sheath meningioma, brain cancer, optic nerve tumor, carcinoma, oral carcinoma, carcinoma in situ, osteosarcoma, carcinosarcoma, ovarian cancer, cartilage tumor, pancoast tumor, cementoma, papillary thyroid carcinoma, myeloid sarcoma, paraganglioma, chondroma, pinealoblastoma, chordoma, pinealocytoma, choriocarcinoma, pituitary tumor, choroid plexus papilloma, pituitary adenoma, clear-cell sarcoma of the kidney, pituitary tumor, craniopharyngioma, plasmacytoma, cutaneous T-cell lymphoma, polyembryoma, cervical cancer, precursor T lymphoblastic lymphoma, colorectal cancer, primary central nervous system lymphoma, Degos' disease, primary effusion lymphoma, desmoplastic small round cell tumor, primary peritoneal cancer, diffuse large B-cell lymphoma, prostate cancer, dysembryoplastic neuroepithelial tumor, pancreatic cancer, dysgerminoma, pharyngeal carcinoma, embryonal carcinoma, peritoneal pseudomyxoma, endocrine gland tumor, renal cell carcinoma, endodermal sinus tumor, renal medullary carcinoma, enteropathy-associated T-cell lymphoma, retinoblastoma, esophageal cancer, rhabdomyomas, fetus-in-fetus, rhabdomyosarcoma, fibroma, Richter's transformation, fibrosarcoma, rectal cancer, follicular lymphoma, sarcoma, follicular thyroid cancer, schwannomatosis, ganglioneuroma, seminoma, gastrointestinal cancer, sertoli cell tumor, germ cell tumor, sex cord-gonadal stromal tumor, gestational choriocarcinoma, signet ring cell carcinoma, giant cell fibroblastoma, skin cancer, giant cell tumor of bone, small blue round cell tumor, glial tumor, small cell carcinoma, glioblastoma multiforme, soft tissue sarcoma, glioma, somatostatinoma, gliomatosis cerebri, soot wart, glucagonoma, spinal tumor, gonadoblastoma, splenic marginal zone lymphoma, granulosa cell tumor, squamous cell carcinoma, gynandroblastoma, synovial sarcoma, gallbladder carcinoma, Sezary's disease, gastric cancer, small intestine cancer, hairy cell leukemia, squamous cell carcinoma, hemangioblastoma, stomach cancer, head and neck cancer, T-cell lymphoma, hemangiopericytoma, testicular cancer, hematological malignancy, hepatoblastoma, thyroid cancer, hepatosplenic T-cell lymphoma, transitional cell carcinoma, Hodgkin's lymphoma, throat cancer, non-Hodgkin's lymphoma, urachal carcinoma, invasive lobular carcinoma, urogenital cancer, intestinal cancer, urothelial carcinoma, kidney cancer, uveal melanoma, laryngeal cancer, uterine cancer, lentigo maligna, verrucous carcinoma, lethal midline carcinoma, visual pathway glioma, leukemia, vulvar cancer, testicular stromal tumor, vaginal cancer, liposarcoma, Waldenstrom's macroglobulinemia, lung cancer, adenolymphoma, lymphangioma, nephroblastoma and lymphangiosarcoma.

Preferably, the cancer is selected from the group consisting of bladder cancer, breast cancer, cervical cancer, colon cancer (including colorectal cancer), esophageal cancer, head and neck cancer, liver cancer, lung cancer (small cell lung cancer and non-small cell lung cancer), melanoma, myeloma, neuroblastoma, ovarian cancer, pancreatic cancer, prostate cancer, kidney cancer, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, melanoma, nasopharyngeal carcinoma, neuroendocrine carcinoma, ovarian cancer, renal cancer, salivary gland cancer, spindle cell cancer-induced metastasis, non-Hodgkin's lymphoma, Hodgkin's lymphoma, as well as hematological malignancies, such as acute myeloid leukemia (AML), acute lymphoblastic leukemia (ALL), diffuse large B-cell lymphoma (DLBCL), follicular lymphoma (FL), chronic lymphocytic Leukemia (CLL), chronic myelogenous leukemia (CML), mantle cell lymphoma (MCL).

Most preferably, the cancer is small cell lung cancer (SCLC).

A third aspect of the invention relates to a combination product for preventing and/or treating a disease, in which the combination product comprises a Bcl-2 inhibitor and a chemotherapeutic agent, the disease is selected from the group consisting of cancer. Further, the cancer includes, but is not limited to, those cancers as described in the second aspect of the invention in the above detailed description of the invention.

In some embodiments, the Bcl-2 inhibitor is a compound (e.g, Compound I-A), or a pharmaceutically acceptable salt or solvate thereof, as specifically described in the first aspect of the invention.

In some embodiments, the combination product is in the form of a pharmaceutical composition.

In some embodiments, the Bcl-2 inhibitor and the chemotherapeutic agent are each in a separate preparation.

In some embodiments, the Bcl-2 inhibitor and the chemotherapeutic agent are administered simultaneously or sequentially.

In some embodiments, the Bcl-2 inhibitor and the chemotherapeutic agent may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the combination product of the invention comprising the Bcl-2 inhibitor and the chemotherapeutic agent in the form of a pharmaceutical composition (preferably, each in a separate dosage unit form), as desired, can be daily administered for, including but not limited to: 1 time, 2 times, 3 times, 4 times, 5 times or 6 times.

In some embodiments, the combination product of the invention comprising the Bcl-2 inhibitor and the chemotherapeutic agent in the form of a pharmaceutical composition (preferably, in the form of a dosage unit), as desired, can be daily administered for, including but not limited to: 1 time, 2 times, 3 times, 4 times, 5 times or 6 times.

In some embodiments, the combination product can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or a pharmaceutically acceptable salt or solvate thereof, and the chemotherapeutic agent or a pharmaceutically acceptable salt or solvate thereof, are administered in a daily amount as described in details in the first aspect of the invention.

A fourth aspect of the invention relates to a method of preventing and/or treating a disease comprising administering to a subject in need thereof a prophylactically and/or therapeutically effective amount of a Bcl-2 inhibitor and a chemotherapeutic agent, in which the disease is cancer. Further, the cancer includes, but is not limited to, those cancers as described in the second aspect of the invention in the above detailed description of the invention.

In some embodiments, the Bcl-2 inhibitor is a compound (e.g, Compound I-A), or a pharmaceutically acceptable salt or solvate thereof, as specifically described in the first aspect of the invention.

In some embodiments, the Bcl-2 inhibitor and the chemotherapeutic agent is in the form of a pharmaceutical composition.

In some embodiments, the Bcl-2 inhibitor and the chemotherapeutic agent are each in a separate preparation.

In some embodiments, the Bcl-2 inhibitor and the chemotherapeutic agent are administered simultaneously or sequentially.

In some embodiments, the Bcl-2 inhibitor and the chemotherapeutic agent may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor and the chemotherapeutic agent of the invention in the form of a pharmaceutical composition (preferably, each in a separate dosage unit form), as desired, can be daily administered for, including but not limited to: 1 time, 2 times, 3 times, 4 times, 5 times or 6 times.

In some embodiments, the Bcl-2 inhibitor and the chemotherapeutic agent of the invention in the form of a pharmaceutical composition (preferably, in the form of a dosage unit), as desired, can be daily administered for, including but not limited to: 1 time, 2 times, 3 times, 4 times, 5 times or 6 times.

In some embodiments, the Bcl-2 inhibitor and the chemotherapeutic agent can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor is administered daily at a dose of 0.017 mg/kg, 0.083 mg/kg, 0.17 mg/kg, 0.33 mg/kg, 0.5 mg/kg (30 mg per day for a 60 kg subject), 0.67 mg/kg, 0.83 mg/kg, 1 mg/kg, 1.16 mg/kg, 1.33 mg/kg, 1.5 mg/kg, 1.67 mg/kg, 2.5 mg/kg, 3.33 mg/kg, 4.17 mg/kg, 5 mg/kg, 5.83 mg/kg, 6.67 mg/kg, 7.5 mg/kg, 7.67 mg/kg, 7.83 mg/kg, 8 mg/kg, 8.12 mg/kg (487 mg per day for a 60 kg subject), 8.16 mg/kg, 8.33 mg/kg, 9.17 mg/kg, 10 mg/kg, 10.83 mg/kg, 11.66 mg/kg, 12.5 mg/kg, 13.33 mg/kg, 14.17 mg/kg, 15 mg/kg, 15.83 mg/kg, 16.67 mg/kg, and a range between the respective amounts, for example, 0.017 mg to 16.67 mg/kg, 0.083 mg to 16.67 mg/kg, 0.17 mg to 16.67 mg/kg, 0.33 mg to 16.67 mg/kg, 0.5 mg to 15 mg/kg, 0.5 mg to 13.33 mg/kg, 0.5 mg to 11.67 mg/kg, 0.5 mg to 10 mg/kg, 0.5 mg to 8.33 mg/kg, 0.5 mg to 8.16 mg/kg, 0.5 mg to 8.12 mg/kg, etc.; and the daily dose of the chemotherapeutic drug, such as topotecan, is 0.001 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg (in Example, topotecan, mice, 1 mg/kg/12.3), 0.09 mg/kg, 0.1 mg/kg, 0.5 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 300 mg/kg, 350 mg/kg, 400 mg/kg, 450 mg/kg, 500 mg, and a range between the respective amounts, for example, 0.001 mg to 500 mg/kg, 0.005 mg to 500 mg/kg, 0.01 mg to 500 mg/kg, 0.05 mg to 500 mg/kg, 0.08 mg to 500 mg/kg, 0.08 mg to 400 mg/kg, 0.08 mg to 300 mg/kg, 0.08 mg to 200 mg/kg, 0.08 mg to 100 mg/kg, 0.08 mg to 50 mg/kg, 0.08 mg to 10 mg/kg, 0.08 mg to 1 mg/kg, 0.08 mg to 0.5 mg/kg, 0.08 mg to 0.1 mg/kg and so on.

Lastly, WO 2018/027097 is incorporated by reference herein, in its entirety and for all purposes.

SPECIFIC MODELS FOR CARRYING OUT THE INVENTION

The present invention will be further illustrated by the following examples and control examples. However, it should be understood that these examples and control examples are merely used to explain the invention in more details, but not intend to limit the present invention.

Example 1. General Experimental Methods Used in the Invention (1) WST Experiment Anti-proliferative effect was detected by CCK-8 (Cell Counting Kit-8) based on water-soluble tetrazolium salt (WST) (Ishiyama M, Tominaga H, Shiga M et al., A combined assay of cell viability and in vitro cytotoxicity with a highly water-soluble tetrazolium salt, neutral red and crystal violet. Biol. Pharm. Bull 19 (11) 1518-1520 (1996), Vol. 19, No. 11; and, Tominaga H, Ishiyama M, Ohseto F et al., A water-soluble tetrazolium salt useful for colorimetric cell viability assay. Anal. Commun., 1999, 36, 47-50.). Cells were inoculated to 96-well plates and treated with different concentrations of test substances for 72 hours. By acting 9 different concentrations of topotecan (wherein 9 concentrations were selected in a 3× gradient between $10^{-2}$ and $10^{2}$) with 3 different concentrations of Compound 6 for 72 hours, the combination effect of Compound 6 and the drug were tested. Each test dose was tested with 3 replicate wells.

Usually, 9 series of doses of the test substance were selected, and added to 96-well plates, 100 μl/well. For the combination experiment, the final volume of the two test substances is 100 μl/well. Each test dose was tested with 3 replicate wells. On the same plate, 3-6 wells were selected and added with 100 μl of dilution solution as a control group, and another 3-6 wells were used as a blank control. In addition to the blank control wells, 100 μl of the cell suspension was added to each well (containing an appropriate number of cells to ensure that at the time of detection, the cells of the cell control group just covered the bottom of the well) of the same 96-well plate. The culture plate was cultured at 37° C. for 72 hours in a C02 incubator. At the end of the culture, for the adherent cells, the old solution in the well to be tested was removed, and 100 μl/well of CCK-8 test solution (corresponding medium containing 10% CCK-8, 5% FBS) was added. For the suspension cells, 20 μl/well of CCK-8 stock solution was added directly. The plate was continuously incubated at 37° C. for 2-4 h in C02 incubator.

The OD values were measured at A450 nm by a microplate reader (SpectraMax Plus 384, Molecular Devices, LLC., US). Using the average OD value of 3 replicate wells, the percentage of cell viability was calculated by the following formula:

(O.D. of test well−O.D. of blank control well)/(O.D. of cell control well−O.D. of blank control well)×100.

The IC50 was calculated using the nonlinear regression data analysis method of Graphpad Prism 6.0 software.

For the combination test, the cell viability was calculated by normalizing the average OD value of 3 duplicate wells of the single drug control. By comparing the IC50 of the combination curve with the single drug curve, the synergistic effect of two compounds was determined by combining the observation of whether the curve of the combination group was shifted left.

(2) Evaluation Method of In Vivo Pharmacodynamics Experimental

A subcutaneous xenograft tumor model of human tumor immunodeficient mice was established by cell inoculation: tumor cells in logarithmic growth phase were collected, counted and resuspended in 1×PBS, and the cell suspension concentration was adjusted to 2.5-5×107/mL. Using a 1 mL syringe (4 gauge needle), the tumor cells were inoculated subcutaneously in the right side of immunodeficient mice, 5-10×106/0.2 mL/mouse (All animals were purchased from Beijing Vital River Laboratory Animal Technology Co., Ltd. SCXK (Beijing) 2012-0001). All animal experiments were strictly in accordance with the laboratory animal use and management practices of GenePharma Co., Ltd. and Ascentage Pharma Group Co., Ltd. The calculation of relevant parameters referred to the Chinese CFDA "Guidelines for Non-Clinical Research Techniques of Cytotoxic Antitumor Drugs". The NCI-H146 cells used in the Institute were a gift from Professor Wang Shaomeng of the University of Michigan, USA.

Animal body weight and tumor size were measured twice a week during the experiment. The conditions and death of the animals were observed every day. Routine monitoring included the effects of tumor growth and treatment on normal animal behaviors, including activity, feeding and drinking situations, weight gain or loss, eyes, coat and other abnormalities in the experimental animals. The deaths and clinical symptoms observed during the experiment were recorded in the raw data. The entire operations of administration, measurement of mouse body weight and tumor volume were performed in a clean bench. Plasma and tumor tissues were collected, weighed and photographed after the end of the last administration according to the experimental protocol. Plasma and tumor samples were frozen and stored at −80° C.

Tumor volume (TV) was calculated as: TV=a×b2/2, in which a and b represented the length and width of the tumor as measured, respectively. The relative tumor volume (RTV) was calculated as: RTV=Vt/V1, in which V1 was the tumor volume at the time of grouping and administration, and Vt was the tumor volume measured on a day after administration. The evaluation index of anti-tumor activity was the relative tumor proliferation rate T/C (%), which was calculated as: relative tumor proliferation rate T/C (%)=(TRTV/CRTV)×100%, in which TRTV was the RTV of the treatment group, CRTV was the RTV of the vehicle control group; tumor remission rate (%) was calculated as: (the number of SD (stable disease), PR (tumor partial regression) and CR (tumor complete regression) in the tumor-bearing mice after treatment)/the total number of mice in the group× 100%.

Change of body weight %=(measured body weight− body weight at the time of grouping)/body weight at the time of grouping×100%.

Evaluation criteria of therapeutic efficiency: according to the Chinese CFDA "Technical guidelines for non-clinical research on cytotoxic antitumor drugs" (November 2006), it was determined as effective when the T/C (%) value was <40% and statistic analysis showed p<0.05; and a dose of the drug was considered to be severely toxic when the body weight of the mice dropped by more than 20% or the rate of drug-related deaths exceeded 20%.

The synergistic analysis was performed by the following formula 6: synergy factor=((A/C)×(B/C))/(AB/C); A=RTV value of the group administered with A only; B=RTV value of the group administered with B only; C=RTV value of the vehicle control group; AB=RTV value of the group administered with A and B in combination (Clarke R. Issues in experimental design and endpoint analysis in the study of experimental cytotoxic agents in vivo in breast cancer and other models [J]. Breast Cancer Research & Treatment, 1997, 46(2-3): 255-278). If the synergy factor was >1, there was a synergistic effect; if the synergistic factor=1, there was an additive effect; if the synergistic factor<1, there was an antagonistic effect.

Example 2. Preparation of Exemplary Compounds as Bcl-2 Inhibitors (Compounds 3, 6 and 13)

(1) Synthesis of 2-((1H-pyrrolo[2,3-b]pyridin-5-yl) oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl) sulfonyl)benzamide (Compound 3)

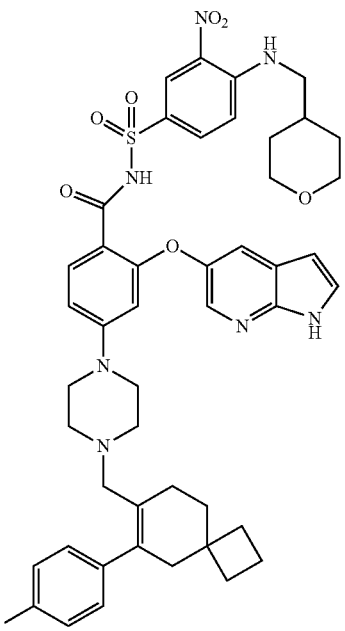

A mixture of 2-((1H-pyrrolo[2,3-b]pyridin-5-yl)oxy)-4-(4-((6-(4-chlorophenyl) spiro[3.5]non-6-en-7-yl)methyl)piperazin-1-yl)benzoic acid (1.75 g, 3 mmol), 3-nitro-4-(((tetrahydro-2H-pyran-4-yl)methyl)amino)benzenesulfonamide (1.43 g, 4.5) reacted in EDCI (1.15 g, 6 mmol) and 4-(N, N-dimethylamino)pyridine (550 mg, 4.5 mmol) and dichloromethane (40 ml) at room temperature overnight, and then water was added. The aqueous layer was extracted with dichloromethane. The combined organic layers were washed with brine, concentrated and purified with silica column to obtain 2-((1H-pyrrolo[2,3-b]pyridil-5-yl)oxy)-4-(4-((6-(4-chlorophenyl)spiro[3.5]non-6-en-7-yl)methyl)piperazin-1-yl)-N-((3-nitro-4-((((tetrahydro-2H-pyran-4-yl)methyl)amino)phenyl)sulfonyl)benzamide (1.7 g, 64.4%) was obtained as a yellow solid.

1H NMR (400 MHz, methanol-d4) δ 8.70 (d, J=2.3 Hz, 1H), 8.01 (d, J=2.7 Hz, 1H), 7.87 (d, J=9.2, 2.3 Hz, 1H), 7.66 (d, J=8.9 Hz, 1H), 7.55 (d, J=2.7 Hz, 1H), 7.47 (d, J=3.4 Hz, 1H), 7.38 (d, J=8.4 Hz, 2H), 7.10 (d, J=8.4 Hz, 2H), 6.97 (d, J=9.2 Hz, 1H), 6.77 (dd, J=8.9, 2.4 Hz, 1H), 6.44 (d, J=3.4 Hz, 1H), 6.34 (d, J=2.4 Hz, 1H), 4.02-3.94 (m, 3H), 3.66 (s, 3H), 3.49-3.38 (m, 2H), 3.41-3.25 (m, 7H), 2.42 (s, 3H), 2.26 (s, 3H), 2.00-1.67 (m, 4H), 1.45-1.38 (m, 2H).

(2) Synthesis of (R)—N-((4-(((1,4-dioxan-2-yl) methyl)amino)-3-nitrophenyl) sulfonyl)-2-((1H-pyrrolo[2,3-b]pyridin-5-yl)oxy)-4-(4-((6-(4-chlorophenyl)spiro[3.5] non-6-en-7-yl) methyl)piperazin-1-yl)benzamide (Compound 13)

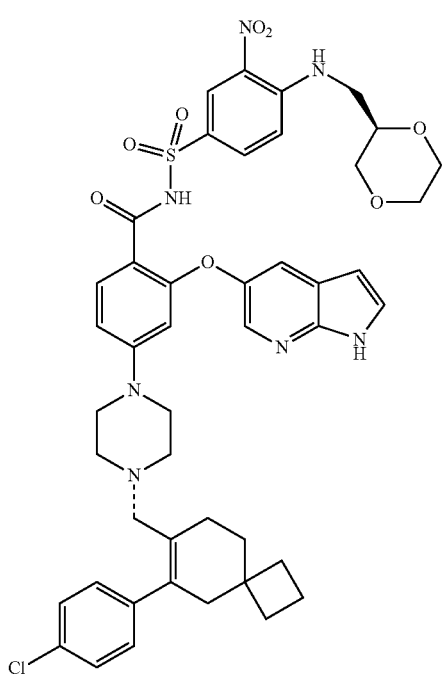

The title compound was prepared in a similar manner to that described for the synthesis of Compound 3.

1H NMR (400 MHz, methanol-d4) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H).

Similarly, Compound 6 was prepared similarly according to the method described for the synthesis of Compound 13, with specific reference to WO 2018/027097.

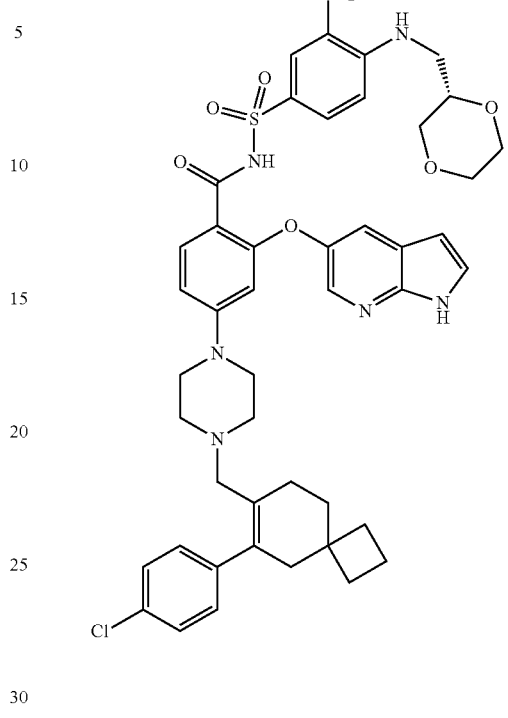

Compound 6

Example 3. Effects of Topotecan Alone or Combination of Topotecan and Compound 6 on Different Malignant Tumor Cells In Vitro Data (1) The experimental method was as described in Section (1) of Example 1. The cell viability (%) values of topotecan alone and the combination of topotecan and Compound 6 in the following malignant tumor cells were determined in the WST experiment: NCI-H146 (small cell lung cancer (SCLC)).

As shown in FIG. 1, in NCI-H146 small cell lung cancer (SCLC), the combination of Compound 6 with the chemotherapeutic agent topotecan enhanced the inhibition effect on the proliferation of tumor cells.

Specifically, in NCI-H146 (SCLC), the IC50 of topotecan alone for proliferation inhibition was 0.127, while the IC50 of topotecan in combination with Compound 6 (0.04 μM, 0.08 μM, 0.12 μM) for the proliferation inhibition were 0.026, 0.022 and 0.023, respectively; in another NCI-H146 (SCLC), topotecan alone inhibited proliferation with an IC50 of 0.068, while topotecan in combination with Compound 6 (0.1 μM, 0.2 μM, 0.4 μM) inhibited proliferation with IC50 of 0.009, 0.013 and 0.008, respectively.

(3) Summary

Thus, when topotecan and Compound 6 in combination was used, the anti-proliferative activity in hematological malignancies was further enhanced in the in vitro experiment. The comparison of IC50 was performed with the curves of combination administration and the curves of single administration, and it was observed that the curves of combination administration shifted to the left. Therefore, the combination of topotecan and Compound 6 had a synergistic effect.

Example 4. Effects of Topotecan Alone and the Combination of Topotecan and Compound 6 in Human NCI-H146 (SCLC) Mouse Xenograft Tumor Model (1) The experimental method was as described in Section (2) of Example 1. In the experiment, the SCLC mouse xenograft tumor model derived from human NCI-H146 tumor cells was established (Gould S E et al. Translational value of mouse models in oncology drug development. Nature medicine. 2015 21, 431-439). When the tumor volume reached 100-200 mm3, randomization was performed according to tumor volume and mouse body weight, and two independent in vivo experiments were performed on the model to evaluate the anti-tumor effects of the combination of Compound 6 and the chemotherapeutic agent TPT (topotecan).

In this experiment, Compound 6 was administered at a dose of 100 mg/kg, p.o., qd; TPT was administered at a dose of 1 mg/kg, p.o., d1-5/w (i.e., a 2-day interval after 5 days of administration). After one week of treatment, the TPT group lost about 5% of body weight. To prevent further weight loss, the TPT administration regimen was adjusted to d1-3/w (i.e, a 4-day internal after 3 days of administration), and continued for one week (study number APS-EF-51-2017-NCI-H146).

(2) Experimental Results

Figure 2:
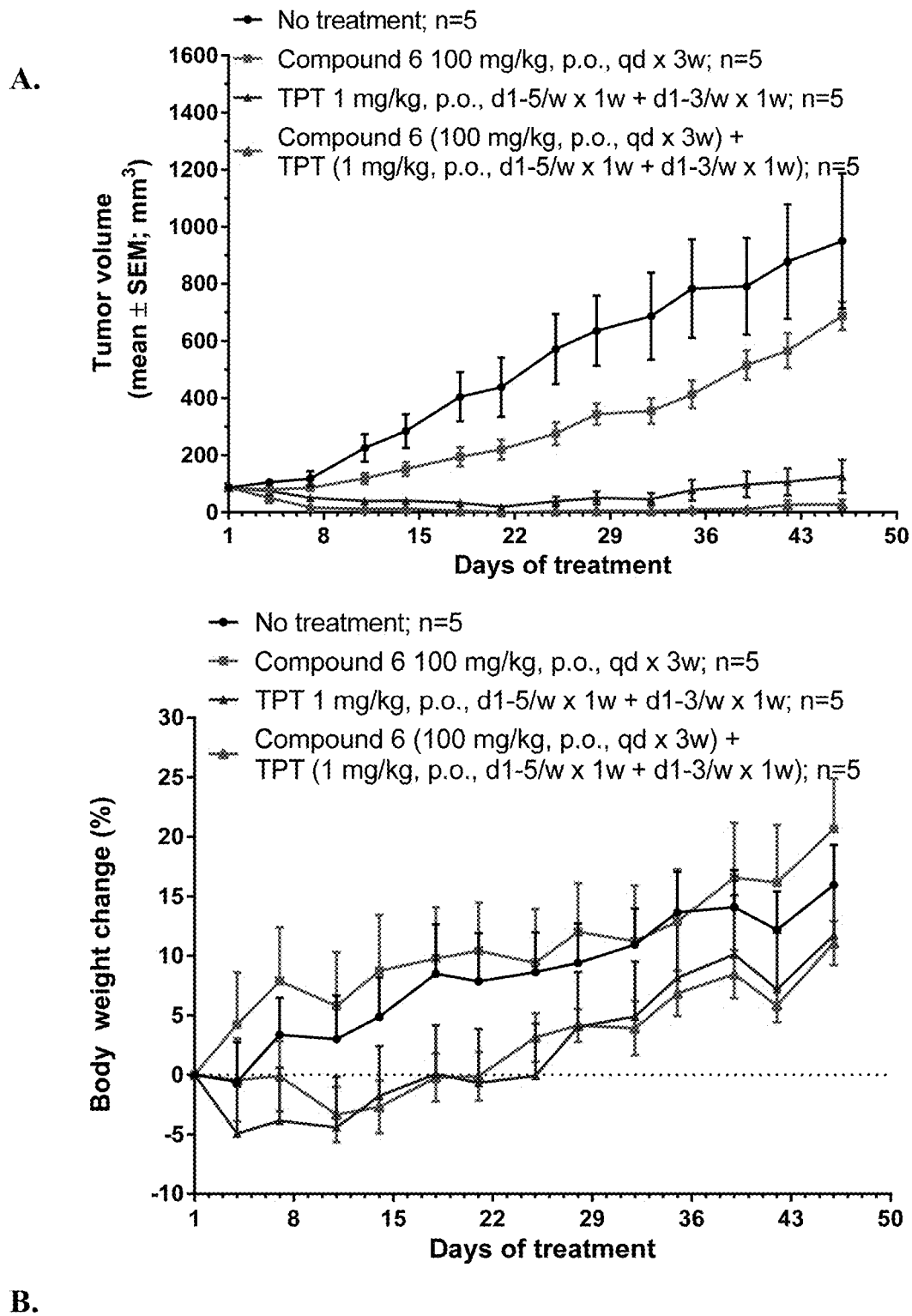
FIG. 2 shows the anti-tumor effect (A) and body weight change of Compound 6 alone or in combination with topotecan in a human NCI-H146 (SCLC) mouse xenograft tumor model.

As shown in FIG. 2A and Table 1, at the end of the administration (i.e., on the 21st day after administration), the Compound 6 alone group showed moderate anti-tumor activity with a T/C value of 49% (P<0.05), and there was no CR, PR or SD (remission rate was 0%). The TPT group showed potent anti-tumor activity with a T/C value of 5% (P<0.01), and among the 5 mice treated with TPT, 2 had CR and 3 had PR (remission rate was 100%). The T/C value of the combination of Compound 6 and TPT reached 0% (P<0.01). At the end of administration, all 5 mice treated with the Combination developed CR (remission rate was 100%). Although there was no statistically significant difference in the RTV values between the combination group and the TPT alone group, the inhibitory effect of the combination on tumor growth was significantly enhanced, with CR appearing in all 5 mice receiving the combination therapy. In the observation after discontinuation (on the 46th day after administration), the remission rates of the Compound 6 alone group, the TPT alone group, and the combination treatment group were changed to 0%, 40% (2/5 CR), and 100% (3/5 CR, 1/5 PR and 1/5 SD), respectively, which further confirmed the continued efficacy of the combination therapy.

TABLE 1

Antitumor effects of Compound 6 alone or in combination with topotecan in human NCI-H146 (SCLC) mouse xenograft tumor model

| Treatment | RTV on day 21 after administration (mean ± standard error) | T/C (%) on day 21 after administration | RTV on day 35 after administration (mean ± standard error) | T/C (%) on day 35 after administration | Tumor remission rate %[a] on day 21 after administration | Tumor remission rate %[a] on day 46 after administration |
|---|---|---|---|---|---|---|
| No-treatment | 5.16 ± 1.05 | — | 9.48 ± 2.00 | — | 0/5CR, 0/5PR, 0/5SD(0%) | 0/5CR, 0/5PR, 0/5SD(0%) |
| Compound 6 100 mg/kg | 2.51 ± 0.25* | 49 | 4.89 ± 0.39 | 52 | 0/5CR, 0/5PR, 0/5SD(0%) | 0/5CR, 0/5PR, 0/5SD(0%) |
| TPT 1 mg/kg | 0.26 ± 0.12** | 5 | 0.77 ± 0.35** | 8 | 2/5CR, 3/5PR, 0/5SD(100%) | 2/5CR, 0/5PR, 0/5SD(40%) |
| Compound 6 + TPT | 0 ± 0**,## | 0 | 0.10 ± 0.07**,## | 1 | 5/5CR, 0/5PR, 0/5SD(100%) | 3/5CR, 1/5PR, 1/5SD(100%) |

*P < 0.05,
**P < 0.01, compared with no treatment group;
P < 0.01, compared with Compound 6 alone group;
[a]remission including CR, PR and SD.

(3) Conclusion:

Compound 6 in combination with TPT had no significant side effects (FIG. 2B) and significantly increased the antitumor effect of TPT monotherapy in the human NCI-H146 (SCLC) mouse xenograft tumor model. Therefore, the combination of Compound 6 and TPT may benefit clinically for patients with small cell lung cancer (SCLC).

What is claimed is:

1. A combination comprising a Bcl-2 inhibitor and a chemotherapeutic agent, wherein the Bcl-2 inhibitor is selected from the group consisting of:

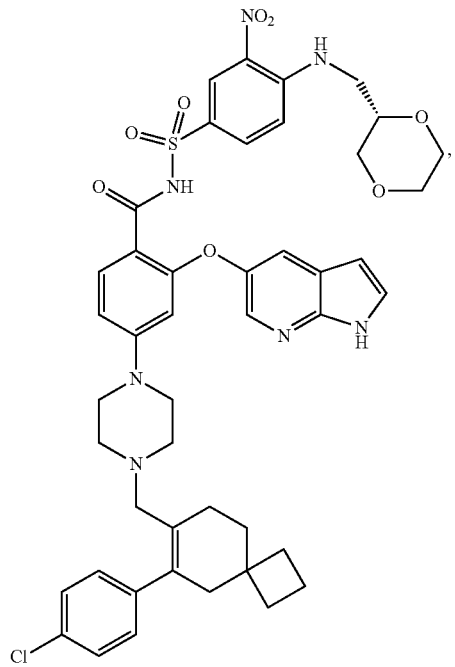 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt thereof, or a solvate thereof, and wherein the chemotherapeutic agent is topotecan, or a pharmaceutically acceptable salt thereof, or a solvate thereof.

2. The combination according to claim 1, wherein the combination product is in the form of a pharmaceutical composition.

3. The combination according to claim 1, wherein the Bcl-2 inhibitor and the chemotherapeutic agent are each in a separate preparation.

4. The combination according to claim 1, wherein the Bcl-2 inhibitor and the chemotherapeutic agent are administered simultaneously or sequentially.

5. The combination according to claim 1, further comprising a pharmaceutically acceptable carrier, diluent, or excipient.

6. The combination according to claim 1, further comprising a tablet, a capsule, a granule, a syrup, a powder, a lozenge, a sachet, a cachet, an elixir, a suspension, an emulsion, a solution, a syrup, an aerosol, an ointment, a cream, or an injection.

7. A method of treating a cancer, comprising administering a Bcl-2 inhibitor and a chemotherapeutic agent to a subject in need thereof, wherein the Bcl-2 inhibitor is selected from the group consisting of:

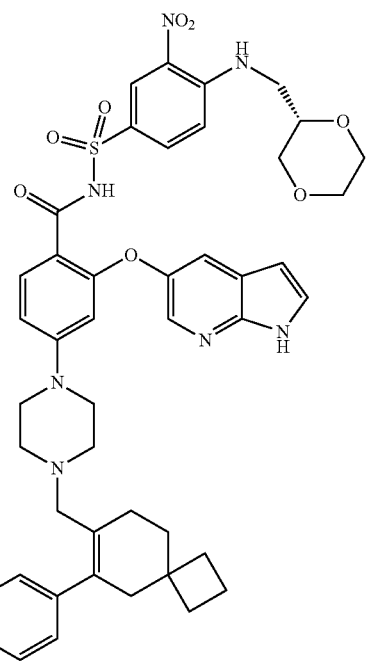

or a pharmaceutically acceptable salt thereof, or a solvate thereof, and wherein the chemotherapeutic agent is topotecan, or a pharmaceutically acceptable salt thereof, or a solvate thereof.

8. The method of claim 7, wherein the cancer is selected from the group consisting of bladder cancer, breast cancer, cervical cancer, colon cancer, colorectal cancer, esophageal cancer, head and neck cancer, liver cancer, lung cancer, small cell lung cancer, non-small cell lung cancer, melanoma, myeloma, neuroblastoma, ovarian cancer, pancreatic cancer, prostate cancer, kidney cancer, sarcoma, osteosarcoma, skin cancer, squamous cell cancer, gastric cancer, testicular cancer, thyroid cancer, uterine cancer, mesothelioma, cholangiocarcinoma, leiomyosarcoma, liposarcoma, melanoma, nasopharyngeal carcinoma, neuroendocrine carcinoma, ovarian cancer, renal cancer, salivary gland cancer, spindle cell cancer-induced metastases, non-Hodgkin's lymphoma, Hodgkin's lymphoma, acute myeloid leukemia (AML), acute lymphoblastic leukemia (ALL), diffuse large B-cell lymphoma (DLBCL), follicular lymphoma (FL), chronic lymphocytic leukemia (CLL), chronic myelogenous leukemia (CML), and mantle cell lymphoma (MCL).

9. The method of claim 7, wherein the cancer is small cell lung cancer (SCLC).

10. The method of claim 7, wherein the Bcl-2 inhibitor or pharmaceutically acceptable salt thereof or solvate thereof is administered in a dose of from about 0.0025 to 1500 mg/day.

11. The method of claim 7, wherein the chemotherapeutic agent or pharmaceutically acceptable salt thereof or solvate thereof is administered in a dose of from about 0.005 mg/day to about 1000 mg/day.

* * * * *